(12) United States Patent
Betz et al.

(10) Patent No.: US 10,206,884 B2
(45) Date of Patent: Feb. 19, 2019

(54) MICROCAPSULES WITH POLYMERIC COATING COMPRISING A LIPID AND AN ACTIVE AGENT

(71) Applicant: FRESENIUS KABI DEUTSCHLAND GMBH, Bad Homburg (DE)

(72) Inventors: Michael Betz, Eichenstätt (DE); Edmundo Brito De La Fuente, Friedrichsdorf (DE); Crispulo Gallegos-Montes, Bad Homburg (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/106,476

(22) PCT Filed: Dec. 19, 2014

(86) PCT No.: PCT/EP2014/078616
§ 371 (c)(1),
(2) Date: Jun. 20, 2016

(87) PCT Pub. No.: WO2015/091885
PCT Pub. Date: Jun. 25, 2015

(65) Prior Publication Data
US 2017/0000741 A1 Jan. 5, 2017

(30) Foreign Application Priority Data
Dec. 20, 2013 (EP) .................... 13199066

(51) Int. Cl.
*A61K 9/50* (2006.01)
*A61K 9/16* (2006.01)
(Continued)

(52) U.S. Cl.
CPC ............... *A61K 9/50* (2013.01); *A23L 29/10* (2016.08); *A23L 29/231* (2016.08);
(Continued)

(58) Field of Classification Search
None
See application file for complete search history.

(56) References Cited

U.S. PATENT DOCUMENTS 5,008,118 A * 4/1991 Iwanami ............. A61K 9/1617
424/450
5,840,860 A * 11/1998 Annison .................. A21D 2/16
436/71

(Continued)

FOREIGN PATENT DOCUMENTS

| WO | 2001/037812 | 5/2001 | |
|---|---|---|---|
| WO | 2005/030173 | 4/2005 | |
| WO | WO 2010060914 A1 * | 6/2010 | ............. A23K 40/30 |

OTHER PUBLICATIONS

Das et al., "Zinc-pectin-chitosan composite particles for drug delivery to the colon: Role of chitosan in modifying in vitro and in vivo drug release", International Journal of Pharmaceutics 406 (2011) pp. 11-20.*

(Continued)

*Primary Examiner* — Ernst V Arnold
*Assistant Examiner* — Kyung S Chang
(74) *Attorney, Agent, or Firm* — Hylton-Rodic Law PLLC

(57) ABSTRACT

The present invention relates to microcapsules and to methods for them. The microcapsules comprise a polymeric coating that is at least partly crosslinked with a polymeric matrix comprising a polysaccharide. In the matrix, a lipid and an active agent or a prodrug or salt thereof are embedded, the lipid preferably having a melting point of at least 30° C. The microcapsules can be used as a medicament, dietary supplement or food additive, the microcapsules comprising a polymeric coating that is at least partly crosslinked with a polymeric matrix comprising a polysaccharide. As above, a lipid and an active agent or a prodrug or salt (Continued)

Figure 1:
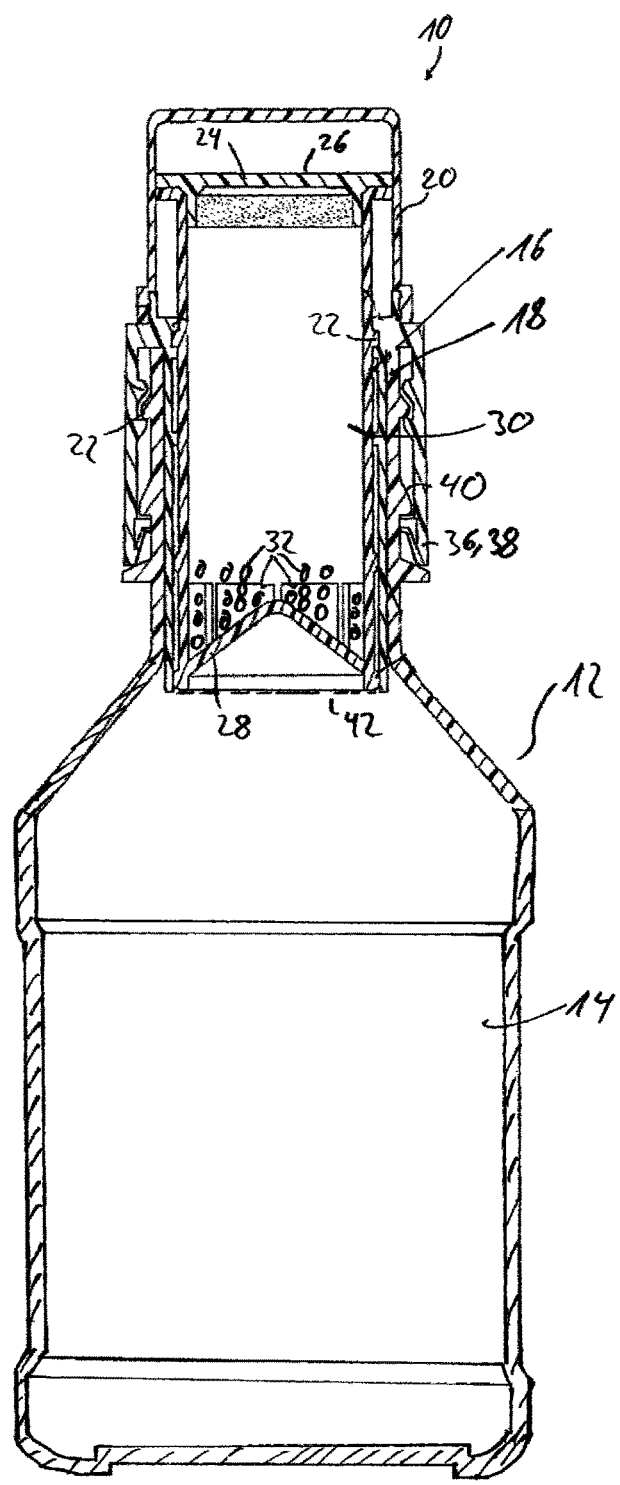

thereof are embedded in the matrix, with the lipid preferably having a melting point of at least 30° C. Methods for treating diarrhea or preventing colon cancer comprising administering such microcapsules are also disclosed.

19 Claims, 6 Drawing Sheets

(51) Int. Cl.
    *A23L 29/231*     (2016.01)
    *A23L 33/115*     (2016.01)
    *A23P 10/35*     (2016.01)
    *B01J 13/14*     (2006.01)
    *A23L 29/10*     (2016.01)
    *A61K 31/19*     (2006.01)
    *B65B 7/28*     (2006.01)
    *B65D 47/06*     (2006.01)
    *B65D 51/28*     (2006.01)

(52) U.S. Cl.
    CPC ............ *A23L 33/115* (2016.08); *A23P 10/35* (2016.08); *A61K 9/5036* (2013.01); *A61K 9/5089* (2013.01); *A61K 31/19* (2013.01); *B01J 13/14* (2013.01); *B65B 7/28* (2013.01); *B65D 47/06* (2013.01); *B65D 51/28* (2013.01); *A61K 9/16* (2013.01)

(56) References Cited

U.S. PATENT DOCUMENTS

2007/0065379 A1*   3/2007   Biatry .................. A61K 8/11
                                                             424/59
2012/0141531 A1*   6/2012   Coulter ................ A61K 9/107
                                                           424/236.1

OTHER PUBLICATIONS

Banasiewicz et al., "Clinical aspects of sodium butyrate application in dietary treatment of bowel disease", Review paper, Przegląd Gastroenterologiczny 2010; 5 (6): 329-334 (Year: 2010).*

Krokowicz et al., "Microencapsulated sodium butyrate administered to patients with diverticulosis decreases incidence of diverticulitis—a prospective randomized study", Int J Colorectal Dis (2014) 29:387-393 and on-line publication date is Dec. 18, 2013 (Year: 2013).*

Lorenzo-Lamosa, et al. "Design of microencapsulated chitosan microspheres for colonic drug delivery," Journal of Controlled Release, Elsevier, Amsterdam, vol. 52. No. 1-2, Mar. 1998: pp. 109-118.

* cited by examiner

MICROCAPSULES WITH POLYMERIC COATING COMPRISING A LIPID AND AN ACTIVE AGENT

CROSS REFERENCE TO RELATED APPLICATIONS

This application is a U.S. national stage application of International Application No. PCT/EP2014/078616, filed on Dec. 19, 2014, which claims priority to European Application No. 13199066.5, filed on Dec. 20, 2013. The contents of these previously filed applications are hereby incorporated by reference herein in their entirety.

The present invention relates to microcapsules and to methods for preparing the same, the microcapsules comprising a polymeric coating, the polymeric coating being at least partly crosslinked with a polymeric matrix comprising a polysaccharide, wherein in the matrix a lipid and an active agent or a prodrug or salt thereof are embedded, the lipid preferably having a melting point of at least 30° C.

Furthermore, the present invention relates to microcapsules for use as a medicament, the microcapsules comprising a polymeric coating, the polymeric coating being at least partly crosslinked with a polymeric matrix comprising a polysaccharide, wherein in the matrix a lipid and an active agent or a prodrug or salt thereof are embedded, the lipid preferably having a melting point of at least 30° C.

Further, the present invention relates to the use of microcapsules comprising a polymeric coating, the polymeric coating being at least partly crosslinked with a polymeric matrix comprising a polysaccharide, wherein in the matrix a lipid and an active agent or a prodrug or salt thereof are embedded, the lipid preferably having a melting point of at least 30° C. as dietary supplement or food additive. The present invention further relates to a method for treating or preventing colonic disorders, in particular for treating diarrhoea or preventing colon cancer, the method comprising administering such microcapsules.

BACKGROUND OF THE INVENTION

Drug delivery systems that specifically deliver active agents to the colon have been recognized as having important therapeutic advantages. It is contemplated in the art that a large number of colonic conditions could be treated more effectively with a lower risk of adverse side reactions if the respective active agent were only released locally, i.e. in the colon or the respective part of the colon. Examples of such colonic disorders include Crohn's disease, ulcerative colitis, colorectal cancer, constipation and diarrhea. Further such drug delivery systems are described to be beneficial for patients in cases where delay in absorption is necessary.

WO 2008/059062 A1 for example describes drug delivery systems that can deliver therapeutic and/or diagnostic agents to the colon. These systems include pectin beads crosslinked with zinc or other divalent cations, wherein these beads are then coated with specific polymers, i.e. polyacrylates. These beads are prepared by dropping the pectin solution which contains the dispersed drug into a curing solution containing zinc cations. Similarly, WO 2009/092333 relates to a device for the process of preparing sodium alginate/chitosan slow release capsules. These systems do not contain any lipids or lipophilic drugs embedded in the beads.

Among the active agents known for the treatment of colonic conditions, short chain fatty acids (SOFA) and in particular butyrate and its derivatives have been described in the literature. These methods described in the literature apply different strategies for delivering the respective short chain fatty acids to the colon.

For example EP 2 289 505 describes a nutritional composition which consists of a core of probiotics, a prebiotic support, a butyric acid compound and one or more gastro-resistant coatings. The composition is used in form of tablets to target the probiotics to the colon and the butyric acid compound is contained in the composition to improve the absorption of probiotics in the intestine.

WO 2010/060914 describes the microencapsulation of butyric acid within a lipid matrix using a spray cooling process. The microcapsules are prepared for animal or human consumption and are intended to protect the butyric acid compound from the acidic gastric environment and increase the absorption on the intestinal level. However, the described digestion tests indicate that only a small part of the microencapsulated butyric acid compounds are in fact delivered to the colon. Similar microcapsules are described e.g. in EP 1 354 520 with the same limitation as described above.

Besides the microencapsulation of butyric acid, some documents describe a prodrug-based strategy using butyric acid esters of carbohydrates. For example U.S. Pat. No. 5,840,860 describes a delivery system for short chain fatty acids which consists of a polysaccharide to which short chain fatty acids are bound by means of an ester or amide bond to generate short chain fatty acid prodrugs. The polysaccharides and the amide or ester bonds within the prodrug are described not to be cleaved in the stomach or small intestine but only by microbial enzymes in the colon. The dose of butyric acids which is actually released in the colon can, however, only hardly be defined because the delivery depends amongst others on the activity of the enzymes in the gut.

Thus, there is still a need for advantageous delivery systems being adapted to deliver active agents, in particular lipophilic or water-insoluble active agents, to the colon.

SUMMARY OF THE INVENTION

The present invention relates to microcapsules comprising a polymeric coating, the polymeric coating being at least partly crosslinked with a polymeric matrix comprising a polysaccharide, wherein in the matrix a lipid and an active agent or a prodrug or salt thereof are embedded.

Furthermore the present invention relates to a method for preparing microcapsules, and microcapsules obtained or obtainable by said method, wherein each microcapsule comprises a polymeric coating, the polymeric coating being at least partly crosslinked with a polymeric matrix comprising a polysaccharide, wherein in the matrix a lipid and an active agent or a prodrug or salt thereof are embedded, the method comprising
(a) providing an aqueous solution comprising the polymer being comprised in the coating
(b) providing an aqueous composition comprising the polysaccharide,
(c) forming an oil phase comprising the lipid and the active agent or prodrug or salt thereof, preferably by heating the oil phase to the melting temperature of the lipid or above, preferably for a time in the range of from 1 min to 1 h
(d) mixing the oil phase according to (c) with the aqueous composition according to (b) thereby forming an emulsion,
(e) adding the emulsion according to (d) drop-wise to the solution according to (a) thereby forming the microcapsules, (f) isolating the microcapsules and drying of the isolated microcapsules.

In a further aspect, the present invention relates to microcapsules, as described above, for use as a medicament and the use of the microcapsules as dietary supplement or food additive, in particular for use in preventing and/or treating colon cancer and/or diarrhoea. Likewise, the present invention relates to a method for treating diarrhoea or preventing colon cancer comprising administering at least one microcapsule, as described above, to a patient in need thereof.

In a further aspect, the present invention relates to a container comprising a container body defining a first chamber for holding a liquid and comprising an opening, a container cap mounted at the opening of the container body, wherein the container cap comprises a dispensing mechanism comprising a closed end, an open end and a second chamber defined there between holding at least one microcapsule, as described above and below, wherein the dispensing mechanism is movable between a storage position, wherein the second chamber is sealed off from the first chamber, and an activated position, wherein the microcapsule is allowed to be dispensed into the first chamber.

Further, the present invention relates to the said container for providing a liquid dispensed composition, comprising the steps:
(i) providing the container body with the first chamber holding a liquid,
(ii) mounting the cap to the opening of the container body with the second chamber holding at least one microcapsule, and
(iii) activating the dispensing mechanism so as to move from the storage position to the activated position such that at least one microcapsule is dispensed into the first chamber of the container body so as to form the liquid dispensed composition.

DETAILED DESCRIPTION

It was surprisingly found that microcapsules comprising a polymeric coating which is at least partly crosslinked with a polymeric matrix comprising a polysaccharide, wherein in the matrix a lipid and an active agent or a prodrug or salt thereof are embedded, are surprisingly stable and capable of delivering active agents to the colon.

The Polymeric Matrix

As described above, the polymeric matrix comprises a polysaccharide. Any polysaccharide known to those skilled in the art and being suitable for pharmaceutical applications may be employed. The polysaccharide may, for example, be a neutral or an ionic polysaccharide, such as an anionic or cationic polysaccharide.

As used herein, the term "ionic polysaccharide" refers to a polysaccharide comprising monomeric units having an acidic functional group, such as a carboxyl, sulfate, sulfonate, phosphate or phosphonate group, or a basic functional group, such as an amino, substituted amino or guanidyl group. In aqueous solution at a suitable pH range or in the presence of a base or a metal salt, an ionic polysaccharide comprising acidic functional groups is present as polyanion, and such a polysaccharide is referred to herein as an "anionic polysaccharide". Likewise, in aqueous solution at a suitable pH range or in the presence of an acid or a metal salt, an ionic polysaccharide comprising basic functional groups will be a polycation. Such a polysaccharide is referred to herein as a "cationic polysaccharide". As used herein, the terms ionic polysaccharide, anionic polysaccharide and cationic polysaccharide thus refers to polysaccharides in which the acidic or basic functional groups are not charged, as well as polysaccharides in which some or all of the acidic or basic functional groups are charged, in combination with a suitable counterion.

By way of example, the following suitable anionic polysaccharides are mentioned: alginate, pectin, xanthan, gum arabic, carrageenan, gellan, gum karaya, tragacanth, cassia gum, dextran sulfate, carboxymethylcellulose, hyaluronic acid, polyglucuronic acid, polymanuronic acid, polygalacturonic acid, polyarabinic acid; chrondroitin sulfate and dextran phosphate.

Suitable cationic polysaccharides include chitosan, trimethlyated chitosan, cationic guar gum, cationic hydroxyethylcellulose, aminodextran and dimethylaminodextran.

The term "nonionic polysaccharide", as used herein, refers to a polysaccharide which does not comprise monomeric units having ionizable functional groups (except for the optionally oxidized reducing end of the polysaccharide), such as acidic or basic groups. Such a polysaccharide will be uncharged in aqueous solution. Examples of suitable nonionic polysaccharides are agar, arabinoxylans, curdlan, beta-glucan, guar gum, locust bean gum, tara gum, glucomannan, pullulan, starch, modified starches like hydroxyalkyl starch, hydroxypropylstarch, hydroxyethlystarch, cellulose and modified celluloses like alkylcelluloses, such as $C_1$-$C_6$-alkyleelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, and ethylhydroxyethylcellulose.

Preferably, the polysaccharide is selected from the group of pectins, alginates, carrageenans, xanthan, gellan, tragacanth, hyaluronic acid, gums, celluloses, starches, agar, arabinoxylans, curdlan, beta-glucan, glucomannans, pullulan, chondroitin sulfate, dextrans, chitosans, aminodextran and dimethylaminodextran and derivatives of the aforementioned polysaccharides. It is to be understood that the polymeric matrix may also comprise a mixture of two or more of the aforementioned polysaccharides.

The term "derivative" in this context includes naturally occurring derivatives as well as derivatives obtained or obtainable by chemical modification such as single or multiple substitution of the polysaccharide, by oxidation, by reduction or the like.

According to a preferred embodiment, the polysaccharide is an anionic polysaccharide. In this case, the polymer present in the polymeric coating is preferably a cationic polymer so that the crosslinking may be achieved, e.g. via electrostatic interactions. Alternatively, the polymer present in the polymeric coating is an anionic polymer. In this case crosslinking is preferably achieved via electrostatic interactions via multivalent ions, such as in particular divalent metal ions as described hereinunder in detail.

Preferably, the polysaccharide is selected from the group consisting of alginate, pectin, xanthan, gum arabic, carrageenan, gellan, gum karaya, tragacanth, cassia gum, dextran sulfate, carboxymethylcellulose, hyaluronic acid, polyglucuronic acid, polymanuronic acid, polygalacturonic acid, polyarabinic acid; chrondroitin sulfate and dextran phosphate.

Preferably, the molecular weight of the polysaccharide is in the range of from 1 to 1000 kDa, more preferably in the range of from 10 to 500 kDa, more preferably from 20 to 100 kDa.

Preferably, the polysaccharide is a pectin or a derivative thereof. As used herein the term "pectin" is known to those skilled in the art and refers to a family of complex polysaccharides. Pectin is one compound or main compound in the intercellular layer and cell walls of higher plants. Pectins generally have a backbone consisting of linear polymers of galacturonic acid and some branches of neutral sugars. Commercially available pectins are derived from a variety of fruits or vegetable sources, mainly apple and citrus fruits. The carboxyl groups of the polygalacturonic acids are typically partly esterified, such as with methanol.

Thus, the present invention also relates to microcapsules, as described above, wherein the polymeric matrix comprises a pectin or a derivative thereof.

Likewise, the present invention relates to a method, as described above, as well as to microcapsules obtained or obtainable by said method, wherein the polymeric matrix comprises a pectin or a derivative thereof.

Preferably, the polysaccharide is a low methoxyl pectin. The term "low methoxyl pectin" refers to a type of pectin that has been partially de-esterified. The degree of esterification (DE) or degree of methylation (DM) is defined as the percentage of methylated galacturonic acids based on the total amount of galacturonic acids in a pectin molecule. Theoretically, the degree of esterification can range from 0% to 100%. Pectins with a degree of esterification (DE) of higher than 50% are known as high methoxyl pectins (HMP), and consequently, low methoxyl pectins (LMP) have a degree of esterification of 50% or less. Preferably, the pectin is a pectin having a DE in the range of 10% to 40%, more preferably in the range of from 15% to 35%, more preferably in the range of 20% to 32%, more preferably in the range of from 25% to 30%.

More preferably, the polysaccharide is an amidated low methoxyl pectin. The term "low methoxyl amidated pectin" refers to a type of low methoxyl pectin in which some of the methyl ester groups have been converted to amide groups. The degree of amidation (DA) is defined as the percentage of amidated galacturonic acid groups, based on the total amount of galacturonic acid groups present. Typically, the degree of amidation is below 25%. More preferably, the amidation degree is in the range of from 1% to 25%, more preferably in the range of from 15% to 25%, more preferably in the range of from 20% to 25% and in particular around 22%.

Thus, the present invention also relates to microcapsules, as described above, wherein the polymeric matrix comprises an amidated low methoxyl pectin.

Preferably, the molecular weight of the pectin is in the range of from 1 to 1000 kDa, more preferably in the range of from 10 to 500 kDa, more preferably from 20 to 100 kDa, more preferably from 30 to 70 kDa.

Likewise, the present invention relates to a method, as described above, as well as to microcapsules obtained or obtainable by said method, wherein the polymeric matrix comprises an amidated low methoxyl pectin.

Besides the polysaccharide the polymer matrix may comprise further components such as, for example, further polymers, such as polysaccharides, and/or plasticizers and/or at least one crosslinking compound as described hereinunder and above. Exemplary polymers include but are not limited to poly(acrylic)- and/or poly(metacrylic) acids (e.g. carbopol, carbomer), poly(methyl vinyl ether/maleic anhydride) copolymers, and their mixtures and copolymers. Exemplary plasticizers include but are not limited to polyethylene glycol, propylene glycol, glycerol or citric acid derivatives.

Preferably, at least 50% by weight, more preferably at least 60% by weight, more preferably at least 70% by weight, more preferably at least 75% by weight, more preferably at least 80% by weight, more preferably at least 85% by weight, more preferably at least 90% by weight, more preferably at least 95% by weight, more preferably at least 96% by weight, more preferably at least 97% by weight, more preferably at least 99% by weight of the polymeric matrix consist of polysaccharides, more preferably of pectin or a mixture of different pectins, more preferably of amidated low methoxy pectins.

Most preferably, the polymeric matrix consists of the at least one crosslinking compound, as described hereinunder, and the polysaccharide, more preferably of the at least one crosslinking compound and a pectin, more preferably of the at least one crosslinking compound and a low methoxy pectin, most preferably of the at least one crosslinking compound and an amidated low methoxy pectin.

Preferably, each of the microcapsules, as described above, or the microcapsules obtained or obtainable by the above-described method comprises the polysaccharide, more preferably the pectin, more preferably, the low methoxy pectin, most preferably the amidated low methoxy pectin, in an amount of from 10 to 50% by weight, preferably of from 20 to 45% by weight, preferably of from 25 to 35% by weight, based on the total weight of the microcapsule.

The Polymeric Coating

As described above, the microcapsules comprise a polymeric coating.

Preferably, this polymeric coating is essentially non-digestible by human enzymes present in the upper gastrointestinal tract. The term "essentially non-digestible" refers to a coating which essentially remains undigested in the upper gastrointestinal tract and the small intestine and thus ensures that the microcapsule comprising the active agent reaches the large intestine. The term "undigested" is denoted to mean that the coating is not digested by acids or enzymes present in the human upper gastrointestinal tract and in the small intestine.

Preferably, the coating is not digested in the human gastrointestinal tract and the small intestine and remains stable until reaching the colon. The term "is not digested in the human gastrointestinal tract and the small intestine and remains stable until reaching the colon" is denoted to mean that at least 50%, more preferably at least 60% of the active agents present in the microcapsules, more preferably at least 65%, more preferably at least 70%, more preferably at least 75%, more preferably at least 80%, more preferably at least 85%, more preferably at least 90%, more preferably at least 95% by weight, most preferably essentially all of the active agent present in the microcapsules reaches the large intestine (the colon) and is not released in the upper gastrointestinal tract.

Thus, the microcapsule is preferably being adapted so that the active agent is not released in the upper gastrointestinal tract and the small intestine. The term "is not released in the upper gastrointestinal tract and the small intestine" is denoted to mean that less than 50%, preferably less than 40%, more preferably less than 35%, more preferably less than 30%, more preferably less than 25%, more preferably less than 20%, more preferably less than 15%, more preferably less than 10%, more preferably less than 5% and most preferably about 0% by weight of the active agent is released in the upper gastrointestinal tract and the small intestine.

Preferably, the microcapsule is thus adapted so that the release of the active agent takes place in the colon, as already described above.

By way of example, the polymer coating may comprise at least one polymer selected from the group consisting of poly-amino saccharides, polymethacrylates, trimethlyated chitosan, cationic guar gum, cationic hydroxyethylcellulose, cassia gum, methyl acrylate-methacrylic acid copolymers, methyl methacrylate-methacrylic acid copolymers, pectins, alginates, carrageenans, xanthan, gellan, tragacanth, hyaluronic acid, gums, gum arabic, celluloses, starches, agar, arabinoxylans, curdlan, beta-glucan, glucomannans, pullulan , chondroitin sulfate, dextrans, aminodextran, dextran sulfate, carboxymethylcellulose, hyaluronic acid, polyglucuronic acid, polymanuronic acid, polygalacturonic acid, polyarabinic acid, dextran phosphate dimethylaminodextran, cellulose acetate succinate, agar, arabinoxylans, curdlan, beta-glucan, guar gum, locust bean gum, tara gum, glucomannan, pullulan, starch, modified starches like hydroxyalkyl starch, hydroxypropylstarch, hydroxyethlystarch, cellulose and modified celluloses like alkylcelluloses, such as $C_1$-$C_6$-alkyleelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, and ethylhydroxyethylcellulose.

It is to be understood that the polymer present in the polymeric coating may, for example, be a neutral or an ionic polymer, such as an anionic or cationic polymer.

As used herein, the term "ionic polymer" refers to a polymer comprising monomeric units having an acidic functional group, such as a carboxyl, sulfate, sulfonate, phosphate or phosphonate group, or a basic functional group, such as an amino, substituted amino or guanidyl group. In aqueous solution at a suitable pH range or in the presence of a base or a metal salt, an ionic polymer comprising acidic functional groups will be a polyanion, and such a polymer is referred to herein as an "anionic polymer". Likewise, in aqueous solution at a suitable pH range or in the presence of an acid or a metal salt, an ionic polymer comprising basic functional groups will be a polycation. Such a polymer is referred to herein as a "cationic polymer". As used herein, the terms ionic polymer, anionic polymer and cationic polymer thus refers to polymers in which the acidic or basic functional groups are not charged, as well as polymers in which some or all of the acidic or basic functional groups are charged, in combination with a suitable counterion.

By way of example, the following suitable cationic polymers are mentioned: poly-amino saccharides, polymethacrylates, trimethlyated chitosan, cationic guar gum, cationic hydroxyethylcellulose, aminodextran and dimethylaminodextran.

By way of example, the following suitable anionic polymers are mentioned: alginate, pectin, xanthan, gum arabic, carrageenan, gellan, gum karaya, tragacanth, cassia gum, dextran sulfate, carboxymethylcellulose, hyaluronic acid, polyglucuronic acid, polymanuronic acid, polygalacturonic acid, polyarabinic acid; chrondroitin sulfate and dextran phosphate.

The term "nonionic polymer", as used herein, refers to a polymer which does not comprise monomeric units having ionizable functional groups, such as acidic or basic groups. Such a polymer will be uncharged in aqueous solution. Examples of suitable nonionic polymers are agar, arabinoxylans, curdlan, beta-glucan, guar gum, locust bean gum, tara gum, glucomannan, pullulan, starch, modified starches like hydroxyalkyl starch, hydroxypropylstarch, hydroxyethlystarch, cellulose and modified celluloses like alkylcelluloses, such as $C_1$-$C_6$-alkyleelluloses, including methylcellulose, ethylcellulose and n-propylcellulose; substituted alkylcelluloses, including hydroxy-$C_1$-$C_6$-alkylcelluloses and hydroxy-$C_1$-$C_6$-alkyl-$C_1$-$C_6$-alkylcelluloses, such as hydroxyethylcellulose, hydroxy-n-propylcellulose, hydroxy-n-butylcellulose, hydroxypropylmethylcellulose, and ethylhydroxyethylcel lulose.

According to a preferred embodiment, the polymer is a cationic polymer. In this case, the polysaccharide present in the matrix is a cationic or an anionic polysaccharide, as described hereinabove. Preferably, the polymer present in the polymeric coating and the polysaccharide of the polymeric matric differ from each other.

In particular, the polymer coating comprises a poly-amino saccharide, more preferably chitosan.

The term "chitosan" as used herein includes any chitosan such as chitosan isolated from natural sources, or commercially available modified or unmodified chitosan. As is well known in the art, chitosan is conventionally produced by de-acetylation of chitin and various grades of chitosan having different average molecular weight and different extents of de-acetylation can be prepared. Thus, the term "chitosan" as used herein includes chitosan with complete or nearly complete de-acetylation (such as 90 to 100% de-acetylation) or equally chitosan with less than complete de-acetylation. The term "chitosan" also includes derivatives of chitosan, such as chitosan modified by chemical reaction. Preferably, the molecular weight (kDa) of the chitosan is in the range of from 1 to 1000, more preferably in the range of from10 to 900 kDa, more preferably from 50 to 700, more preferably from 75 to 500, and most preferably in the range of from 100 to 250.

According to a preferred embodiment of the invention, the chitosan has a degree of de-acetylation in the range of from 70% to 95%, more preferably in the range of from 80% to 90%, most preferably around 85%. Preferably, the viscosity of a 1% solution of the chitosan in 1% acetic acid at 20° C. is in the range of from 1 to 3000 mPas, more preferably in the range of from 50 to 500 mPas, most preferably in the range from 70 to 150 mPas (measured on a Brookfield DV-II+ Pro viscosimeter at 20° C. using spindle 61 at a rotational speed of 30 rpm).

Preferably, at least 70% by weight of the coating, more preferably at least 80% by weight of the coating, more preferably at least 90% by weight of the coating, more preferably at least 95% of the coating consists of a polymer selected from the group consisting of chitosan, poly-amino saccharides, methyl acrylate-methacrylic acid copolymers, cellulose acetate succinate, hydroxy propyl methyl cellulose phthalate, hydroxy propyl methyl cellulose acetate succinate, methyl methacrylate-methacrylic acid copolymers, sodium alginate and mixtures of two or more thereof, more preferably of a polymer selected from the group consisting of chitosan, trimethlyated chitosan, aminodextran and dimethylaminodextran.

More preferably, at least 70% by weight of the coating, more preferably at least 80% by weight of the coating, more preferably at least 90% by weight of the coating, more preferably at least 95% of the coating consists of chitosan and/or trimethylated chitosan, more preferably of chitosan.

Crosslinking

As described above and below, the polymeric coating present in the microcapsules according to the invention is at least partially crosslinked with the polymeric matrix. The crosslinking between the polymeric coating and the polymeric matrix may be any crosslinking known to those skilled in the art such as a covalent crosslinking between the polymers present in the polymer coating and the polysaccharide present in the polymeric matrix, or a crosslinking via other interactions, such as hydrophobic interactions or hydrogen bonding or via an electrostatic linking between the polymers present in the polymer coating and the polysaccharide of the polymer matrix. Such crosslinking may be achieved chemically or ionotropically by any method known to those skilled in the art.

Preferably, the polymeric coating is crosslinked with the matrix, preferably with the polysaccharides present in the matrix via electrostatic interactions. Preferably, the polysaccharide comprised in the matrix is a cationic polysaccharide or an anionic polysaccharide and the polymer present in the polymer comprised in the polymeric coating is the opposite that is either anionic or cationic, so that the polymer comprised in the coating and the polysaccharide comprised in the matrix are crosslinked via electrostatic interactions. Preferably, the polysaccharide comprised in the matrix is anionic and the polymer comprised in the coating is cationic. More preferably, the polysaccharide comprised in the matrix is a pectin and the polymer comprised in the coating is chitosan.

The microcapsules according to the invention may further comprise additional crosslinking compounds. Exemplary crosslinking compounds are metal ions, such as calcium, magnesium, zinc, barium, cobalt, strontium, iron, aluminum, copper, or cadmium ions or chemical crosslinkers such as genipin, glutaraldehyde or azo-crosslinkers or mixtures thereof.

Such crosslinking compounds are preferably present to either crosslink the polysaccharides present in polymeric matrix with themselves and/or to crosslink the polymers present in the coating with themselves.

Preferably the crosslinking compound is a cationic crosslinking compound, more preferably a multivalent cationic crosslinking compound. Preferably, the crosslinking compound is a metal ion, in particular a multivalent metal ion.

According to a preferred embodiment, the polysaccharide comprised in the matrix is anionic and the crosslinking compound is a cationic crosslinking compound, in particular a metal ion. In this case, the crosslinking is preferably an electrostatic interaction between the polysaccharide and the crosslinking compound, in particular the metal ion. More preferably the polysaccharides present in the matrix are linked with each other via a multivalent cationic crosslinking compound. More preferably, the metal ions are calcium and/or zinc ions.

Thus, the present invention also relates to microcapsules as described above, as well as to microcapsules prepared or obtained or obtainable by the above-described method wherein the polysaccharides present in the matrix are crosslinked with each other and/or with themselves via metal ions, preferably via calcium and/or zinc ions.

More preferably, the polymeric coating is crosslinked with the matrix, which is crosslinked via calcium ions, preferably via calcium ions derived from calcium chloride. Thus, the present invention also relates to microcapsules as described above as well as to microcapsules obtained or obtainable by the above-described method, said microcapsules comprising calcium chloride and/or calcium ions derived from calcium chloride.

Likewise, the polymers present in the polymeric coating may be crosslinked with each other. Similar to the polymeric matrix, the polymers may be crosslinked by any method known to those skilled in the art.

Surprisingly, it has been found that in particular when using divalent cations, in particular calcium, as crosslinking compounds, the microcapsules proved to be particularly stable in the upper gastrointestinal tract and suitable for colon delivery.

The Active Agent

The term "active agent" as used in the context of the present invention refers to any natural or synthetic substance being pharmaceutically active. The term is in particular intended to include active agents which are suitable for treating adverse conditions of the colon, i.e. colonic disorders. In particular, the active agent is an active agent for use in treating or preventing colonic disorders, such as constipation, diarrhea, irritable bowel syndrome, Crohn's disease, ulcerative colitis, cancer and the like.

This includes, laxatives, antidiarrheal drugs, non-steroidal anti-inflammatory drugs, anti-microbials, especially those effective against anaerobic microbes, and cytotoxic agents for the treatment of cancer, in particular colon cancer.

When the microcapsules are used for the treatment of diarrhea, any type of active agent known to those skilled in the art as being suitable for the treatment of diarrhea, may be used. This includes, preferably, antiobiotics, bile acid sequestrants, probiotics, pepto-bismol, codeine, bismuth subsalicylate, crofelemer, atropine, diphenoxylate, magnesium aluminium phyllosilicates, kaolin, zinc, loperamide, simethicone, butyric acid, and prodrugs thereof.

When the microcapsules are used for the treatment of constipation, any type of active agent known to those skilled in the art as being suitable for the treatment of constipation, may be used. This includes, preferably, laxatives and antacids such as picosulfate, sennosides, docusate, methylcellulose, bisacodyl, polycarbophil, phosphates, glycerin, polyethylene glycols, magnesium citrate, magnesium sulfate, sodium sulfate, potassium sulfate, lactulose, lactose, mannitol, sorbitol, castor oil, senna, magnesium oxide or citric acid and chloride channel activators, such as lubiprostone and guanylate cyclase-C agonists such as linaclotide and serotonin receptor agonists such as prucalopride and prodrugs thereof.

When the microcapsules are used for the treatment of Crohn's disease or ulcerative colitis, any type of active agent known to those skilled in the art as being suitable for the treatment of Crohn's disease or ulcerative colitis, may be used. This includes, preferably, anti-inflammatory drugs such as 5-aminosalyciylic acid, sulfasalazine, olsalazin and glucocorticoides such as dexamethasone, budesonide or prednisone/prednisolone, anti-microbials, especially those effective against anaerobic microbes such as methotrexate, and immuno-suppressants such as cyclosporene A and azathioprin.

When the microcapsules are used for the treatment of colon cancer, any type of antitumor agent known to those skilled in the art as being suitable for the treatment of colon cancer can be used. Suitable anti-tumor agents include, for example, antiproliferative agents, agents for DNA modification or repair, DNA synthesis inhibitors, DNA/RNA transcription regulators, RNA processing inhibitors, agents that affect protein expression, synthesis and stability, agents that affect protein localization or their ability to exert their physiological action, agents that interfere with protein—protein or protein-nucleic acid interactions, agents that act by RNA interference, receptor binding molecules of any chemical nature (including small molecules and antibodies), targeted toxins, enzyme activators, enzyme inhibitors, gene regulators, HSP-90 inhibitors, molecules interfering with microtubules or other cytoskeletal components or cell adhesion and motility, agents for phototherapy, and therapy adjuncts.

Some of the active agents described hereinabove and below can be administered in the form of prodrugs. Prodrugs have been widely studied for the colonic targeting of various active ingredients (such as steroid and non-steroid anti-inflammatory drugs, and spasmolytics). Preferably, these prodrugs are capable of releasing the active form of the active ingredient in the colon.

In particular the active agent is an agent for use in treating diarrhoea or preventing colon cancer.

According to a preferred embodiment of the invention, the active agent is a lipophilic active agent. The term "lipophilic active agent" refers to compounds that have greater solubility in lipids than in aqueous media. Preferably, the term "lipophilic active agent" refers to an active agent which has a log P value of greater than 1.0, more preferably a log P value greater than 2.0, wherein the log P value is measured by the distribution behavior of the active agent in a biphasic system such as in the octanol/water partition test. This test involves the measurement of the equilibrium concentration of a dissolved substance in a two-phase system of an octanol and water as well as a chromatographic method and is described in OECD test guideline 107.

Preferably, the active agent is butyric acid or a derivative or prodrug thereof, more preferably a butyric acid derivative, most preferably a lipophilic butyric acid derivative.

It is known that some n-butyric acid compounds have advantageous biological effects on the digestive system, stimulating the growth of the intestinal villi and modifying the development of gastroenteric microorganisms. Butyric acid is a short-chain monocarboxylic fatty acid which is also classified amongst the volatile fatty acids together with acetic acid and propionic acid. Butyric acid has two isomers, n-butyric acid and isobutyric acid. At ambient temperature, n-butyric acid is in liquid form and also has a characteristic rancid butter odor which is noticed by humans and by many animal species even in very low concentrations.

More preferably, the active agent is tributyrin. Tributyrin is a prodrug, i.e. a derivative, of butyric acid causing cell differentiation in vitro in a wide range of neoplastic cells. Tributyrin is advantageous over butyric acid in that it does not have an unpleasant odor or taste and is contemplated to be an even more potent inhibitor of epithelia inflammatory response than sodium butyrate, the sodium salt of butyric acid. Some studies indicate that tributyrin is a more effective and better tolerated anti-inflammatory agent in the treatment of chronic inflammatory bowel diseases. Tributyrin was initially synthesized during the 1920ies. It is commercially available through a number of chemical distributors. Tributyrin is an ester of butyric acid, i.e. an ester composed of butyric acid and glycerol with the IUPAC name 1,3-di(butanoyloxy)propan-2-yl butanoate. Tributyrin is a lipophilic compound which is only poorly soluble in water. Reported log P-values for tributyrin are in the range of from 2.5 to 3.0.

Thus, the present invention also relates to microcapsules comprising a polymeric coating, the polymeric coating being at least partially crosslinked with a polymeric matrix comprising a polysaccharide, wherein in the matrix a lipid and tributyrin are embedded.

Furthermore, the present invention relates to a method for preparing microcapsules and microcapsules obtained or obtainable by said method, wherein each microcapsule comprises a polymeric coating, the polymeric coating being at least partially crosslinked with a polymeric matrix comprising a polysaccharide, wherein in the matrix a lipid and tributyrin are embedded, the method comprising (a) providing an aqueous solution comprising the polymer being comprised in the coating
(b) providing an aqueous composition comprising the polysaccharide,
(c) forming an oil phase comprising the lipid and tributyrin, preferably by heating the oil phase to the melting temperature of the lipid or above, preferably for a time in the range of from 1 min to 1 h,
(d) mixing the oil phase according to (c) with the aqueous phase according to (b) thereby forming an emulsion,
(e) adding the emulsion according to (d) drop-wise to the solution according to (a) thereby forming the microcapsule,
(f) isolating the microcapsules and drying of the isolated microcapsules.

In a further aspect, the present invention relates to microcapsules as described above for use as a medicament or dietary supplement or food additive, in particular for use in preventing or treating colon cancer and/or diarrhea, wherein the microcapsules comprise tributyrin as active agent.

Preferably, each of the microcapsules, as described above, or the microcapsules obtained or obtainable by the above-described method comprises the active agent in an amount of from 1 to 80% by weight, more preferably of from 10 to 70% by weight, more preferably of from 15 to 60% by weight, more preferably of from 20 to 50% by weight, most preferably of from 25 to 35% by weight, based on the total weight of each microcapsule. The amount of the active agent may vary between different microcapsules, however it is preferably essentially the same in all microcapsules.

The microcapsules may comprise at least one further active agent embedded in the matrix in addition to the active agent described above. This at least one further active agent is preferably selected from the active agents mentioned above.

In this case, the amount of all active agents present in the microcapsule is preferably in the range of from 1 to 80% by weight, more preferably of from 10 to 70% by weight, more preferably of from 15 to 60% by weight, more preferably of from 20 to 50% by weight, most preferably of from 25 to 35% by weight, based on the total weight of each microcapsule. The amount of the active agents may vary between different microcapsules, however it is preferably essentially the same in all microcapsules.

Preferably, the microcapsules comprise only one active agent, preferably tributyrin.

The Lipid

As described above, the microcapsules comprise an embedded lipid. The term "lipid" refers to a group of organic compounds that includes, but is not limited to fatty acids, mono-, di- and triacylglycerols, sterols and sterol esters, carotinoids, waxes, tocopherols, glycerophospholipids, glyceroglycolipids, sphingophospholipids and sphingoglykolipids and that is characterized by being insoluble in water, but soluble in many organic solvents. The term includes simple lipids which include fats and oils as well as waxes, compound lipids which include phospholipids and derived lipids such as steroids.

Preferably the lipid is selected from the group consisting of natural, refined or hydrogenated, vegetable oils, animal oils, synthetic oils, and mixtures of two or more thereof, more preferably the lipid is a hydrogenated vegetable oil.

Preferably, the lipid according to the invention comprises an ester of a fatty acid, preferably of a fatty acid having from 6 to 24 carbon atoms.

By way of example, the lipid is selected from the group consisting of coconut oil, palm oil, palm kernel oil, olive oil, sunflower oil, safflower oil, rapeseed oil, corn oil, coconut kernel oil, soya oil, linseed oil, castor oil, sesame oil, wheat germ oil, almond oil, walnut oil, hazelnut oil, argan oil, grape seed oil, cocoa butter, peanut oil, cottonseed oil, false flax oil, poppyseed oil, mustard oil and mixtures of two or more thereof.

Preferably, the lipid has a high melting point, i.e. a melting point greater than 30° C.

Thus, the present invention also relates to microcapsules comprising a polymer coating, the polymer coating being at least partly crosslinked with the polymeric matrix comprising a polysaccharide wherein in the matrix the lipid and an active agent, preferably tributyrin, or a prodrug or a salt thereof are embedded, wherein the lipid has a melting point of at least 30° C. Likewise, the present invention relates to a method for preparing such microcapsules as well as to such microcapsules for use as a medicament, in particular for use in treating diarrhea or preventing colon cancer in a patient in need thereof. Further, the present invention relates to the use of such microcapsules as dietary supplement or food additive.

Surprisingly it has been found that when using a high melting lipid in combination with a lipophilic compound, in particular tributyrin, advantageous microcapsules are provided with which the delivery of the active agent to the colon can be improved and the possible loss of the active agent due to a possible release of the active agent in the upper gastrointestinal and in the small intestine can be diminished. It is contemplated that due to the presence of the high melting lipid, the diffusion of the active agent out of the microcapsule is diminished or even avoided.

Further, it has surprisingly been found, that the microcapsules are particularly advantageous in that any diffusion of the lipid out of the microcapsule is diminished, which diffusion may yield in microcapsules comprising lipids on their surface which potential renders the microcapsules sticky. Thus, with the high melting lipid, particularly stable and easy to handle microcapsules are provided which microcapsules are further advantageous with regard to their ability to target the large intestine.

Preferably, the lipid has a melting point in the range of from 30° C. to 80° C., more preferably in the range of from 35° C. to 50° C., more preferably in the range of from 37° C. to 45° C., and most preferably in the range of from 42° C. to 44° C. Preferably, the lipid crystallizes during cooling in the beta prime crystal form.

Thus, the present invention also relates to microcapsules, as described above and to microcapsules obtained or obtainable by the above described method, wherein the embedded lipid has a melting point of from 30° C. to 80° C., more preferably a melting point of from 37° C. to 45° C.

Most preferably, the lipid consists of hydrogenated cocoglycerides (e.g. Witocan® 42/44, Cremer Oleo GmbH & Co. KG), preferably having from 10-18 carbon atoms.

Preferably, the lipid and the active agent, that is the sum of all active agents, preferably tributyrin, are present in the microcapsules in a weight ratio of from 1:9 to 9:1, more preferably of from 1:9 to 1:1, more preferably of from 1:7 to 1:1, more preferably of from 1:5 to 1:3 and most preferably in a weight ratio of from 1:4.5 to 1:3.5.

Thus, in step (c) of the method described above, preferably an oil phase is formed, said oil phase comprising the lipid and the active agent or prodrug or salt thereof in a weight ratio of from 1:4.5 to 1:3.5, and wherein this oil phase is heated to the melting temperature of the lipid or above, preferably for a time in the range of from 1 min to 1 h. Thus the present invention also relates to a method for preparing microcapsules and microcapsules obtained or obtainable by said method, as described above, the method comprising (c) forming an oil phase comprising the lipid, preferably a lipid having a melting point of at least 30° C., and the active agent or prodrug or salt thereof, preferably tributyrin, preferably by heating the oil phase to melting temperature of the lipid or above, preferably for a time in the range of from 1 min to 1 h, and wherein the oil phase comprises the lipid and the active agent in a weight range of from 1:4.5 to 1:3.5.

Preferably each microcapsule comprises the lipid in an amount of from 0.2 to 72% by weight, more preferably of from 2 to 50% by weight, more preferably of from 3 to 40% by weight, more preferably of from 4 to 25% by weight, more preferably of from 5 to 15% by weight, based on the total weight of each microcapsule.

Further Components

Besides the above mentioned components, the microcapsules described above or the microcapsules obtained or obtainable by the above-described method may additionally comprise further polymers, such as further saccharides and/or further lipids and/or further active agents and/or pharmaceutically acceptable carriers or additives.

As used herein, the term "pharmaceutically acceptable carrier and/or additive" means any non-toxic material that does not interfere with the effectiveness of the at least one active agent present in the microcapsule. Pharmaceutically acceptable carriers include diluents, fillers, salts, buffers, stabilizers, solubilizers, flavoring agents, colorants and other materials which are well known in the art.

Preferably, the microcapsules additionally comprise water, preferably in an amount of less than 60% by weight, more preferably less than 50% by weight, more preferably less than 40% by weight, more preferably less than 35% by weight, based on the total weight of the microcapsule.

Preferably, the microcapsules according to the invention additionally comprise at least one emulsifier. Preferably, the at least one emulsifier is embedded, together with the active agent and the lipid, in the matrix.

Suitable emulsifiers according to the invention include lecithin, phospholipids, stearic acid, acacia, diethanol amine, glyceryl monostearate, lanolin alcohols, monoethanol amine, oleic acid, oleyl alcohol, poloxamer, Pluronics.RTM, (BASF, Parsippany, N.J.), polyoxyethylene 50 stearate, polyoxyl 35, castor oil, polyoxl 10 oleyl ether, polyoxyl 20 cetostearyl ether, polyoxyl 40 stearate, propyleneglycol diacetate, propyleneglycol monostearate, sodiumlauryl sulfate, sodium stearate, polyoxyethylene stearates, polysorbates, ammonium phosphatides, sodium, potassium, calcium and magnesium salts of fatty acids, mono- and diglycerides of fatty acids, acetic acid esters of mono- and diglycerides of fatty acids, lactic acid esters of mono- and diglycerides of fatty acids, citric acid esters of mono- and diglycerides of fatty acids, mono- and diacetyl tartaric acid esters of mono- and diglycerides of fatty acids, mixed acetic and tartaric acid esters of mono- and diglycerides of fatty acids, sucrose esters of fatty acids, sucroglycerides, polyglycerol esters of fatty acids, polyglycerol polyricinoleate, propane-1,2-diol esters of fatty acids, thermally oxidised soya bean oil interacted with mono- and diglycerides of fatty acids, stearoyl-2-lactylates, sorbitan esters, methyl glucose sesquistearate, poly alkylene glycol ethers.

Preferably, the microcapsules comprise a phospholipid. Within the meaning of the present invention, the term "phospholipid" refers to a lipid or glyceride that contains a phosphate group. Thus, the phospholipid may be, for example, lecithin, phosphatidylethanol amine, phosphatidylinositol, phosphatidyl serine, diphosphatidyl glycerol (cardiolipin), dilauroylphosphatidyl choline, dimyristoylphosphatidyl choline, dipalmitoylphosphatidyl choline, distearoylphosphatidyl choline, dioleoylphosphatidyl choline, dimyristoylphosphatidylethanol amine, dipalmitoylphosphatidylethanol amine, dipalmitoylphosphatidyl glycerol, dimyristoylphosphatidic acid, dipalmatioylphosphatidic acid, diplamitoylphosphatidyl serine, diplamitoylsphingomyelin, 1-stearic acid-2-plamitoylphosphatidyl choline, polyethylene glycol-2-stearoylphosphatidylethanole amine, and the like.

Preferably, the amount of emulsifier present in each microcapsules, more preferably of the phospholipid, is in the range of from 0% by weight to 20% by weight, more preferably in the range of from 1% by weight to 10% by weight, more preferably in the range of from 1.5% by weight to 2.5% by weight, based on the total weight of each microcapsule.

According to a preferred embodiment of the invention the microcapsules comprise at least one phospholipid as emulsifier, more preferably at least lecithin. Within the meaning of the present invention, the term "lecithin" refers to naturally occurring or synthetic lecithin which may be suitably refined. Suitable lecithins include, but are not limited to, lecithins derived from egg or soy bean. Further suitable lecithins include, but are not limited to, dihexanoyl-L-alpha-lecithin, dioctanoyl-L-alpha-lecithin, didecanoyl-L-alpha-lecithin, didodecanoyl-L-al-pha-lecithin, ditetradecanoyl-L-alpha-lecithin, dihexadecanoyl-L-alpha-lecithin, dioctadekan-oyl-L-alpha-lecithin, dioleoyl-L-alpha-lecithin, dilinoleoyl-L-alpha-lecithin and alpha-palmitol.

Lecithins are typically mixtures of diglycerides or fatty acids linked to the choline ester of phosphoric acid and can contain differing amounts of other components depending on the method of isolation. Preferably, the lecithin present in the oil phase according to the invention is obtained from egg yolk or seeds including soy bean and corn, most preferably soy bean using methods known in the art. Lecithin obtained from soy bean is referred to herein as soy bean lecithin. As to the soy bean lecithin, said soy bean lecithin typically comprises at least 50% by weight of phospholipids, more preferably of from 50 to 80% by weight, more preferably of from 55 to 70% by weight and most preferably of from 58 to 65% by weight based on the total weight of the soy bean lecithin. The soy bean lecithin as described above usually comprises phosphatidyl choline, phosphatidylethanol amine, phosphatidylinositol and phosphatidic acid.

Thus, the present invention also relates to microcapsules, as described above, as well as to microcapsules obtained or obtainable by the above described method, additionally comprising lecithin, wherein the lecithin is preferably embedded in the matrix.

Preferably, the amount of lecithin present in each microcapsules, more preferably of the phospholipid, is in the range of from 0.1% by weight to 20% by weight, more preferably in the range of from 1% by weight to 10% by weight, more preferably in the range of from 1.5% by weight to 2.5% by weight, based on the total weight of each microcapsule.

Preferably, the microcapsules according to the invention additionally comprise at least one flavoring agent or flavor extract or at least one sugar or sugar substitute, such as sucrose, fructose, glucose, lactose and/or natural or synthetic sugar substitutes, such as Acesulfame potassium, aspartame, cyclamic acid, cyclamates, isomalt, saccharin, sucralose, alitame, thaumatin, neohesperidin dihydrochalcone, steviol glycosides, xylitol, sucralose and others.

Further, the microcapsules according to the invention may comprise additionally at least one antioxidant, such as sodium ascorbate, calcium ascorbate, potassium ascorbate, ascorbyl palmitate, ascorbyl stearate, tocopherol concentrate (natural), dl-alpha-tocopherol (synthetic), gamma-tocopherol (synthetic), delta-tocopherol (synthetic), propyl gallate, octyl gallate, dodecyl gallate, erythorbic acid, sodium erythorbate, erythorbin acid, sodium erythorbin, tert-butylhydroquinone, butylated hydroxyanisole (BHA), butylated hydroxytoluene (BHT).

Further, the microcapsules according to the invention may comprise additionally at least one colorant, such as curcumins, turmeric, riboflavins, riboflavin, tartrazine, alkannin, chrysoine resorcinol, Quinoline Yellow WS, Yellow 2G, Sunset Yellow FCF, cochineal, carmines, Citrus red 2, orcein, orchil, azorubine, carmoisine, amaranth, Brilliant Scarlet 4R, Ponceau 4R, Ponceau SX, Scarlet GN, erythrosine, Red 2G, Allura red AC, Indanthrene blue RS, Patent blue V, indigo carmine, indigotine, Brilliant blue FCF, chlorophylls, chlorophylls and chlorophyllins copper complexes, Green S, Fast green FCF, caramels, Brilliant Black BN (Black PN), Carbon black, Brown FK, Chocolate Brown HT, carotenes, annatto extracts, paprika oleoresin (paprika extract), lycopenes, beta-apo-8'-carotenal (C 30), beta-apo-8'-carotenic acid ethyl ester, flavoxanthin, luteins, tagetes extract, Kryptoxanthin, Rubixanthin, Violaxanthin, Rhodoxanthin, Canthaxanthin, Zeaxanthins, beet red, anthocyanins, grape skin extract, blackcurrant extract, purple corn colour, Red cabbage colour, Gardenia yellow, Gardenia blue, Sandalwood, titanium dioxide, iron oxides, aluminium, silver, gold, Lithol Rubine, tannins, orchil.

Physical Parameters

The microcapsules described above or the microcapsules obtained or obtainable by the above-described method preferably have a mean particle size in the range of from 0.1 to 5 mm, more preferably in the range of from 0.8 to 1.5 mm, more preferably in the range of from 1.1 to 1.3 mm, measured using a digital caliper.

Method

As described above, the present invention also relates to a method for preparing a microcapsule comprising a polymeric coating, the polymeric coating being at least partially crosslinked with a polymeric matrix comprising a polysaccharide, wherein in the matrix a lipid and an active agent or prodrug or salt thereof are embedded, the lipid preferably having a melting point of at least 30° C., and the method comprising the steps (a) to (g) as described above.

Step (a)

In step (a) of the method according to the invention, an aqueous solution comprising the polymer being comprised in the coating is provided.

Preferably, the polymer is mixed with an aqueous medium, preferably dissolved in an aqueous medium.

The term "aqueous medium" as used in this context is denoted to mean a medium comprising at least 70% by weight of water, more preferably 75% by weight of water, more preferably 80% by weight of water, more preferably 85% by weight of water, more preferably at least 90% by weight of water based on the total weight of the aqueous medium excluding the polymer present therein. Besides water, the aqueous medium thus may comprise a suitable polar organic solvent such as polar protic solvents like organic acids or alcohols or polar aprotic solvents such as ketones, DMF, DMSO or THF. Preferably, the aqueous medium is a buffer, optionally comprising at least one organic solvent as described above, more preferably comprising no organic solvent. As suitable buffers, e.g. sodium citrate buffer, sodium acetate buffer, sodium phosphate buffer, sodium carbonate buffer, sodium borate buffer and the like are mentioned by way of example.

Preferably, the pH of the aqueous solution provided in step (a) is in the range of from 1 to 7, more preferably of from 2 to 6, more preferably of from 3 to 4, and most preferably around 3.5, most preferably 3.5. The pH may be adjusted by addition of a suitable acid or base, such as, for example organic carboxylic acids such as formic acid, acetic acid, propionic acid, citric acid, lactic acid or inorganic acids such as hydrochloric acid or sulfuric acid, or a base such as sodium hydroxide potassium hydroxide or ammonium. More preferably, the pH is adjusted with acetic acid. Thus, the present invention also relates to a method as described above further comprising adjusting the pH of the solution to a pH of from 1 to 6, more preferably to a pH of from 3 to 4, preferably using acetic acid.

In step (a) of the invention, further suitable compounds may be added. In particular a precursor of the at least one crosslinking compound, as mentioned above, most preferably a divalent metal salt such as a zinc salt or a calcium salt, more preferably a calcium salt, most preferably calcium chloride, is added.

Preferably, the aqueous solution according to step (a) is prepared by mixing all components of the solution stepwise or all together to the aqueous medium at a temperature in the range of from 0° C. to 40° C., more preferably at a temperature in the range of from 10° C. to 30° C., more preferably at a temperature in the range of from 15° C. to 25° C. During step (a), the temperature may be varied or may be held essentially constant.

Preferably, a homogenous solution is prepared by stirring and/or homogenizing the resulting mixture, such as in particular stirring at high speed.

It is to be understood that step (a) may further comprise additional steps such as filtration of the solution after the mixing of the components. Preferably, no filtration is carried out.

Step (b)

In step (b) according to the method described above, an aqueous composition comprising the polysaccharide is provided. The term "aqueous composition" as used in this context is denoted to mean a composition comprising an aqueous medium, the medium comprising at least 70% by weight of water, more preferably 75% by weight of water, more preferably 80% by weight of water, more preferably 85% by weight of water, more preferably at least 90% by weight of water based on the total weight of the aqueous medium. Besides water, the aqueous medium thus may e.g. comprise a suitable polar organic solvent such as polar protic solvents like organic acids or alcohols or polar aprotic solvents such as ketones, DMF, DMSO or THF.

Preferably, the aqueous medium in step (b) is water.

Preferably, the aqueous composition according to step (b) is prepared by heating the aqueous medium to a temperature of at least 30° C., more preferably of at least 40° C., more preferably of at least 50° C., more preferably of at least 60° C., more preferably of at least 70° C., more preferably of at least 80° C., and more preferably of at least 90° C., prior to addition of the polysaccharide. Preferably, the polysaccharide is then added to the aqueous composition, more preferably to the heated aqueous composition, and suitably mixed. The mixing may be carried out by any suitable method known to those skilled in the art, preferably by stirring and/or homogenization. Preferably, the mixture is stirred by high speed. More preferably, the mixture is stirred at high speed until the mixture is homogeneous.

According to preferred embodiments, step (b) further comprises heating of the composition to a temperature of at least 30° C., more preferably of at least 40° C., more preferably of at least 50° C., more preferably of at least 60° C., more preferably of at least 70° C., more preferably of at least 80° C., more preferably of at least 90° C., more preferably to the boiling temperature of the aqueous composition. The heating is preferably carried out for a time in the range of from 1 min to 15 min, more preferably 2 min to 10 min, and most preferably around 5 min. The temperature during this heating step may be varied or held essentially constant. The composition according to step (b) preferably comprises the polysaccharide in an amount in the range of from 1 to 20 wt.-%, more preferably 2 to 10 wt.-%, more preferably 3 to 5 wt.-% and most preferably around 4 wt.-%, based on the total amount of the aqueous composition according to step (b).

Thus, the present invention also relates to a method as described above as well as to microcapsules obtained or obtainable by said method, wherein step (b) of the method comprises providing an aqueous composition comprising the polysaccharide, wherein the composition comprises the polysaccharide in an amount in the range of from 2 to 10 wt.-% based on the total weight of the aqueous composition.

It is to be understood that further components may be added to the aqueous composition according to step (b). For example, flavorants, colorants, antioxidants, sugars and/or sugar substitutes, as mentioned above. Preferably, no further components are added in step (b).

Step (c)

As described above, the method according to the invention comprises a step (c), wherein an oil phase comprising the lipid and the active agent or prodrug or salt thereof is formed by mixing the components, preferably including the step of heating the oil phase to the melting temperature of the lipid or above, preferably for a time in the range of from 1 min to 1 h. The mixing may be carried out by any suitable method known to those skilled in the art, such as stirring or the like.

Preferably, the oil phase according to step (c) comprises the active agent in an amount of preferably at least 50% by weight, based on the total weight of the oil phase. More preferably, the oil phase comprises the active agent in an amount of from 55% by weight to 95% by weight, more preferably in an amount in the range of from 75% to 80% by weight, based on the total weight of the oil phase.

Preferably, the oil phase according to step (c) comprises one or more emulsifiers. Suitable emulsifiers are described above.

Preferably, the oil phase comprises a phospholipid, as described above.

Preferably, the amount of emulsifier, preferably a phospholipid, present in the oil phase according to step (c), more preferably of the phospholipid, is in the range of from 1% by weight to 15% by weight, more preferably in the range of from 2% by weight to 10% by weight, more preferably in the range of from 5% by weight to 7% by weight, more preferably around 6% by weight, based on the total weight of the oil phase.

According to a preferred embodiment of the invention the oil phase comprises at least one phospholipid as emulsifier, more preferably at least lecithin. Preferably, the lecithin present in the oil phase according to the invention is obtained from egg yolk or seeds including soy bean and corn, most preferably soy bean using methods known in the art. Lecithin obtained from soy bean is referred to herein as soy bean lecithin.

Thus, the present invention also relates to a method, as described above, as well as microcapsules obtained or obtainable by said method, wherein the oil phase according to step (c) further comprises lecithin, more preferably soy bean lecithin.

As described above, in step (c), the oil phase is preferably heated to the melting temperature of the lipid described above. Preferably, the oil phase comprising the active agent and at least one emulsifier, preferably a phospholipid, more preferably lecithin, is heated to the melting temperature of the lipid or above. Preferably, the lipid has a melting temperature of at least 30° C. Thus, the oil phase is preferably heated to a temperature of at least 30° C., more preferably to a temperature in the range of from 50° C. to 70° C., more preferably to a temperature around 60° C. The heating is preferably carried out for a time in the range of from 30 s to 1 min. The temperature during the heating step may be varied or held essentially constant. During the heating step, the oil phase is preferably stirred.

Step (d)

As described above, the oil phase according to step (c) is mixed with the aqueous phase according to step (b), thereby forming an emulsion. The mixing may be carried out by any process known to those skilled in the art.

Preferably, the mixing is carried out by stirring for a time in the range of 1 min to 1 day, more preferably of from 5 min to 5 h, more preferably of from 10 min to 1 h. Preferably, the mixing step is carried out at a temperature in the range of from 10° C. to 100° C., more preferably 30° C. to 80° C., more preferably 50° C. to 70° C., most preferably at around 60° C. During step (d), the temperature may be varied or held essential constant. Preferably, the step is carried out at ambient pressure of 1013 mbar.

It is to be understood that in step (d), further components may be added. According to a preferred embodiment of the invention, in step (d), at least one emulsifier is added. Thus, preferably, either in step (c) or in step (d) or in both steps, at least one emulsifier is added, wherein in case at least two emulsifiers are added, these emulsifiers may be the same or may be different from each other.

In case an emulsifier is added in step (d), the emulsifier is preferably selected from the emulsifiers mentioned above with respect to step (c). Preferably, the emulsifier optionally added in step (d) is thus a phospholipid, more preferably a lecithin. It is to be understood that thus portions of the lecithin may be added in step (c) as well as in step (d). Preferably, the emulsifier is only added in step (c).

The resulting mixture of the oil phase (c) with the aqueous phase (b), optionally comprising further components such as at least one emulsifier, as described above, is then preferably homogenized by suitable methods known to those skilled in the art. Preferably, the homogenization is carried out with a stirrer and/or a rotor/stator mixer. After mixing at 60° C. the emulsion is preferably cooled to ambient temperature prior to step (e).

Preferably, the resulting emulsion comprises 1% to 10% by weight of the oil phase, based on the total weight of the emulsion, more preferably 2% to 8% by weight, more preferably 3% to 6% by weight, more preferably 4% to 5% by weight, based on the total weight of the emulsion. Preferably, the emulsion comprises the aqueous phase in an amount of 99% by weight to 80% by weight, more preferably 98% to 92% by weight, more preferably 97% to 93% by weight and most preferably 96% to 95% by weight.

Step (e)

In step (e) of the method described above, the emulsion according to step (d) is dropwise added to the, preferably stirred, solution according to step (a) thereby forming the microcapsules. The dropwise addition of the emulsion may be carried out by any suitable method known to those skilled in the art. Preferably, the emulsion droplet formation is either done manually, such as by using a syringe, or by means of a droplet generating device such as a jet-cutter or an atomizing nozzle. Thus, the present invention also relates to a method, as described above, as well as to microcapsules obtained or obtainable by said method, wherein the dropwise addition in step (e) is carried out manually using a syringe or by means of a jet-cutter.

The size of the microcapsules may be adjusted by adjusting the respective droplet sizes which are added in step (e) to the solution according to step (a) and/or by the drying procedure applied in step (f). Preferably, the microcapsules according to the invention have a mean particle size in the range of from 0.1 to 5 mm, more preferably in the range of from 0.5 to 3 mm, more preferably in the range of from 0.8 to 1.5 mm, more preferably in the range of from 1.0 to 1.2 mm, most preferably around 1.1 mm.

It is contemplated that after having dropped the emulsion according to step (d) into the solution according to step (a), a polymeric coating being at least partially crosslinked with the polymeric matrix of the microcapsules is formed.

Preferably, the mixture according to step (a) comprising the dropwise added emulsion according to step (d) is allowed to stand being stirred for a time in the range of from 1 min to 240 min, more preferably of from 5 min to 120 min, more preferably of from 10 min to 60 min, most preferably of from 15 min to 30 min, most preferably around 20 min. Step (e) is preferably carried out at a temperature in the range of from 10° C. to 30° C., preferably of from 20° C. to 25° C., wherein the temperature during step (e) may be varied or held essentially constant.

As described above, preferably, the mixture according to step (a) further comprises at least one metal salt, preferably calcium chloride. It is contemplated that during step (e), the metal cations further crosslink the polymeric matrix with the polymeric coating and/or crosslink the polymeric matrix and/or crosslink the polysaccharides present in the polymeric matrix with each other and crosslink the polymers of the polymeric coating with each other, thereby forming a stable microcapsule.

The stability of the microcapsules may further be adjusted by adjusting the crosslinking time in step (e), i.e. the time for which the solution according to step (a) and the added droplets of the emulsion according to step (d) are allowed to stand before isolating the microcapsules according to step (f) (crosslinking time). It has surprisingly been found that the longer the crosslinking time is, the more stable the microcapsules are.

Step (f)

The method further comprises isolating the microcapsule and drying of the isolated microcapsule.

The isolation of the microcapsule from the solution may be carried out by any suitable method known to those skilled in the art. Preferably, the isolated microcapsules are filtered off from the solution.

The drying is preferably carried out at a temperature in the range of from 20° C. to 100° C., more preferably at a temperature in the range of from 25° C. to 80° C., more preferably in a temperature range from 30 to 60°, most preferably at 50° C. The drying may be carried out by any suitable method and is preferably carried out in an oven. During the drying step, the pressure is preferably in the range of from 0.01 to 1013 mbar, most preferably at 1013 mbar. Preferably, the drying is carried out for a time in the range of from 1 min to 96 h, more preferably for a time in the range of from 1 h to 48 h, more preferably of from 12 to 24 h. In particular, the drying is carried out until the mass of the microcapsules is constant. The term "the mass of the microcapsules is constant" is denoted to mean that the total weight of the microcapsules remains unchanged irrespective of whether the capsule is further dried for a specific time or not.

Preferably, between the isolating of the microcapsules and the drying step (f), the method further comprises a purification step. In this purification step, preferably the isolated microcapsules are washed at least once with a suitable solvent, preferably with water. Preferably, the microcapsules are washed at least twice with water. Between the washing steps, the microcapsules may be optionally dried.

Use

The microcapsules described above or the microcapsules obtained or obtainable by the above-described method are preferably used as a medicament, dietary supplement or food additive. Preferably, the microcapsules are used for preventing and/or treating colon cancer or for use in preventing and/or treating diarrhea. Further, the present invention also relates to a method for treating diarrhea or preventing or treating colon cancer comprising administering at least one microcapsule as described above or at least one microcapsule obtained or obtainable by the above-described method to a patient in need thereof.

The term "preventing" as used herein refers to retaining health with respect to the diseases or disorders referred to herein for a certain period of time in a subject.

The term "cancer" in the context of the present invention refers to a disease of an animal, including man, characterized by uncontrolled growth of a group of body cells (cancer cells). This uncontrolled growth may be accompanied by intrusion into and destruction of surrounding tissue and possible spread of cancer cells to other locations in the body (metastases). It is known to the skilled person that a cancer may reappear after an initial successful treatment (relapse). The present invention also includes the prevention and treatment of such a relapse.

As used herein, the term "diarrhea" includes all types of diarrhea encompassing acute and chronic diarrhea. The term "chronic diarrhea" includes diseases or conditions including Irritable bowel syndrome, Crohn's disease, Ulcerous colitis, Microscopic colitis, Coeliac disease, Hormonal and Carcinoid syndrome, VIPoma, Glucagonoma, Systemic Mastocytosis, Diabetic diarrhea. Preferably, the diarrhea syndrome is a chronic secretory diarrhea or a acute secretory diarrhea.

A patient in need thereof" is denoted to mean a patient afflicted with colon cancer and/or diarrhea. A "patient afflicted with colon cancer" relates to a subject comprising and/or having comprised colon cancer cells, preferably a tumor, in its body.

Thus, a patient afflicted with colon cancer is a subject diagnosed to suffer from colon cancer or is known to have suffered from colon cancer.

According to the present invention, the term "administering" relates to the application of at least one microcapsule according to the present invention to a subject. Preferably, the at least one microcapsule is administered orally or via a feeding-tube.

Preferably, the at least one microcapsule is administered in a dose effective to prevent and/or treat colon cancer and/or diarrhea. The effective dosage for the respective patient depends upon many factors, including the patient's size, body surface area, age, the particular active agent to be administered, sex, time of mode of administration, general health and other drugs which may be administered concurrently. Efficacy can be monitored by periodic assessment by the skilled person.

The at least one microcapsule referred to herein is administered at least once in order to treat or prevent a disease, in particular colon cancer and/or diarrhea. However, the at least one microcapsule may be administered more than once, for example several times a day or several days a week.

Container

FIG. 1 shows a cross-sectional view of a container 10 according to a first embodiment of the present invention. The container 10 comprises a container body 12. The container body 12 may be made of plastics, glass or the like. The container body 12 defines a container chamber 14 holding a liquid. The liquid may be water or another solution such as a solution for human nutrition such as an oral nutritional supplement, a food for special medical purposes or fruit juice. The container chamber 14 comprises a predetermined volume so as to hold a predetermined volume of the liquid such as 100 ml, 250 ml, 500 ml or the like. Needless to say, the volume depends on the respective use of the container 10 such that the volume may be larger or smaller. The container body 12 comprises an opening 16. The opening 16 is provided at a top end 18 of the container body 12. The liquid may be discharged from the container body 12 through the opening 16.

Figure 2:
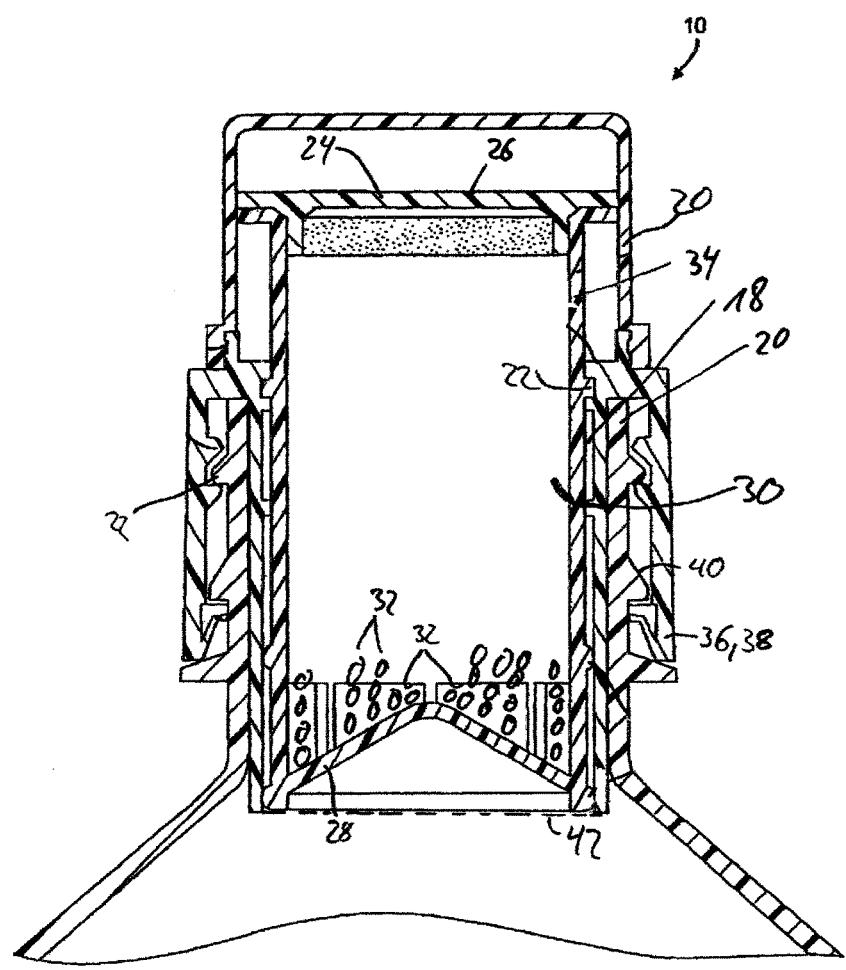

FIG. 2 shows an enlarged partial cross-sectional view of the container 10 according to the first embodiment and of a container cap 20. The container cap 20 may be used with a container 10 such as the one described above. The container 10 may comprise the container cap 20. The container cap 20 is adapted to be mounted at the opening 16 of the container body 12. For example, the container body 12 may comprise a threaded neck 22 to which the container cap 20 is screwed. If the container cap 20 is in use with the container 10, the container cap 20 is mounted to the container body 12. In this case, the container cap 20 closes the opening 16. The container cap 20 comprises a dispensing mechanism 24.

The dispensing mechanism 24 comprises a closed end 26, an open end 28 and a cap chamber 30 defined there between holding at least one microcapsule 32 of the kind as described above. The dispensing mechanism 24 is movable between a storage position, wherein the cap chamber 30 is sealed off, and an activated position, wherein the microcapsule 32 is allowed to be dispensed from the cap chamber 30 as will be explained in more detail below. If the container cap 20 is mounted to the container body 12, the cap chamber 30 is sealed off from the container chamber 14 in the storage position. Further, if the container cap 20 is mounted to the container body 12, the microcapsule 32 is allowed to be dispensed into the container chamber 14 in the activated position. In the present embodiment, the dispensing mechanism 24 is a plunger 34 adapted to be linearly moveable between the storage position and the activated position. The container cap 20 may comprise a securing mechanism 36 adapted to prevent an unwanted activation of the dispensing mechanism 24. For example, the container cap 20 comprises a tamper proof ring 38 that locks behind a collar 40 built into the container body 12 when the container cap 20 is mounted to the container body 12. A rotational motion of the container cap 20 relative to the tamper proof ring 38 provides enough force to break thin protrusions that attach the tamper proof ring 38 to the container cap 20. Thus, the tamper proof ring 38 may be disengaged and the dispensing mechanism 24 is ready to be activated.

The container 10 further comprises a sealing member 42 disposed adjacent the open end 16. Thus, the cap chamber 30 is separated from the container chamber 14 by means of the sealing member 42. The sealing member 42 is integrally formed with the dispensing mechanism 24. Alternatively, the sealing member 42 may be separately formed from the dispensing mechanism 24. The sealing member 42 may be disc-shaped. The sealing member 42 may be a foil or an elastomeric member having a small height if compared with the diameter thereof. The sealing member 42 is adapted to be removed from the open end 16 if the dispensing mechanism 24 is moved to the activated position. More particularly, the sealing member 42 is adapted to be broken if the dispensing mechanism 24 is moved to the activated position.

The container 10 is used to provide a liquid dispensed composition as will be explained in more detail hereinafter. First, the container body 12 is provided. The container chamber 14 holds a liquid as mentioned above. The cap 20 is mounted to the opening 16 of the container body 12 with the cap chamber 30 holding at least one microcapsule 32 as mentioned above. Then, the dispensing mechanism 24 is activated so as to move from the storage position to the activated position such that the at least one microcapsule 32 is dispensed into the container chamber 14 of the container body 12 so as to form the liquid dispensed composition. As mentioned above, the dispensing mechanism 24 is a plunger 34. The dispensing mechanism 24 is activated by means of a linear force. For example, an operator such as patient of the container 10 pushes the plunger 34 at the closed end 26 thereof such that the plunger 34 is linearly moved towards the container body 12. Thereby, the plunger 34 breaks the sealing member 42 and the microcapsule 32 is dispensed into the liquid stored within the container chamber 14. Thus, the liquid dispensed composition is provided.

After the dispensing mechanism 24 is activated and the liquid composition is provided, the cap 20 is removed. The liquid dispensed composition is now adapted to be orally administered through the opening 16 of the container body 12. For example, the liquid dispensed composition is adapted to be drunk out of the container 10 by a patient in need thereof.

Figure 3:
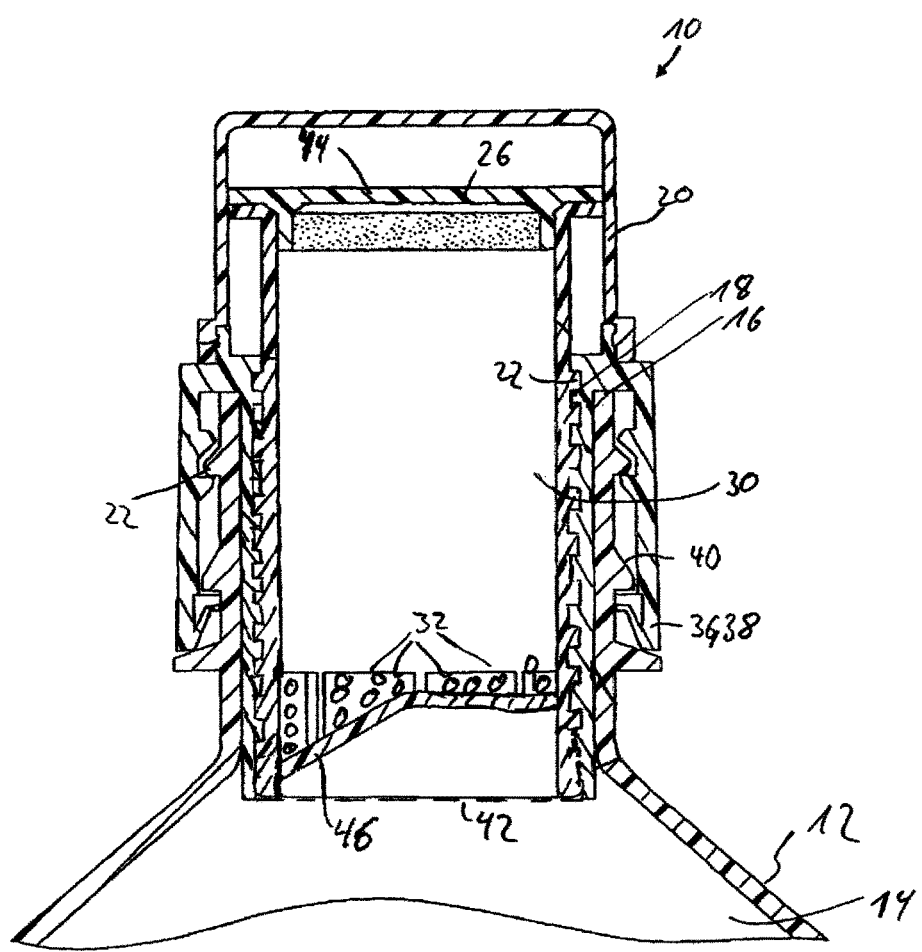

FIG. 3 shows an enlarged partial cross-sectional view of a perspective view of a container 10 according to a second embodiment of the present invention and a cap 20. Hereinafter, only the differences from the first embodiment are described and like constructional members are indicated by like reference numerals.

According to the second embodiment, the dispensing mechanism 24 is a knob 44 adapted to be rotated. For example, the patient rotates the knob 44. The knob 44 comprises a blade member 46 adapted to cut the sealing member 42 if the dispensing mechanism 24 is moved to the activated position. Thus, the dispensing mechanism 24 is activated by means of a rotational force.

In the following especially preferred embodiments, are mentioned by way of example:

1. Microcapsules comprising a polymeric coating, the polymeric coating being at least partly crosslinked with a polymeric matrix comprising a polysaccharide, wherein in the matrix a lipid and an active agent or a prodrug or salt thereof are embedded, the lipid preferably having a melting point of at least 30° C.
2. The microcapsules according to embodiment 1, wherein the polysaccharide is selected from the group consisting of pectins, alginates, carrageenans, xanthan, gellan, tragacanth, hyaluronic acid, gums, celluloses, starches, agar, arabinoxylans, curdlan, beta-glucan, glucomannans, pullulan, chondroitin sulfate, dextrans, chitosans, aminodextran and dimethylaminodextran and derivatives of the aforementioned polysaccharides, preferably the polysaccharide is a pectin.
3. The microcapsules according to embodiment 1 or 2, wherein the polysaccharide is a low methoxy pectin, having a DE in the range of 10% to 40%, more preferably in the range of from 15% to 35%, more preferably in the range of 20% to 32%, more preferably in the range of from 25% to 30%.
4. The microcapsules according to embodiment 3, wherein the said low methoxy pectin is an amidated low methoxy pectin with an amidation degree of 11% to 25%, more preferably in the range of from 15% to 25%, more preferably in the range of from 20% to 25% and in particular around 22%.
5. The microcapsules according to any of the embodiments 1 to 4, comprising the polysaccharide in an amount of from 10 to 50% by weight, preferably of from 25 to 35% by weight, based on the total weight of the microcapsule.
6. The microcapsules according to any of the embodiments 1 to 5, wherein the lipid is selected from the group consisting of natural, refined or hydrogenated, vegetable oils, animal oils, synthetic oils, and mixtures of two or more thereof, more preferably the lipid is selected from the group consisting of coconut oil, palm oil, palm kernel oil, olive oil, sunflower oil, safflower oil, rapeseed oil, corn oil, coconut kernel oil, soya oil, linseed oil, castor oil, sesame oil, wheat germ oil, almond oil, walnut oil, hazelnut oil, argan oil, grape seed oil, cocoa butter, peanut oil, cottonseed oil, false flax oil, poppyseed oil, mustard oil and mixtures of two or more thereof.
7. The microcapsules according to any of the embodiments 1 to 6, wherein the embedded lipid has a melting point of from 30° C. to 80° C., more preferably a melting point of from 37° C. to 45° C., and wherein the lipid preferably crystallizes upon cooling in the beta prime crystal form.
8. The microcapsules according to any of the embodiments 1 to 7, comprising the lipid in an amount of from 0.2 to 72% by weight, more preferably of from 2 to 50% by weight, more preferably of from 3 to 40% by weight, more preferably of from 4 to 25% by weight, more preferably of from 5 to 15% by weight, based on the total weight of each microcapsule.
9. The microcapsules according to any of the embodiments 1 to 8, additionally comprising lecithin, wherein the lecithin is preferably embedded in the matrix.
10. The microcapsules according to embodiment 9, comprising the lecithin in an amount of from 0.1 to 20% by weight, preferably 1.5 to 2.5% by weight, based on the total weight of the microcapsule.
11. The microcapsules according to any of the embodiments 1 to 10, wherein the active agent is butyric acid or a prodrug or salt thereof, preferably tributyrin.
12. The microcapsules according to any of the embodiments 1 to 11, comprising the active agent in an amount of from 1 to 80% by weight, most preferably of from 25 to 35% by weight, based on the total weight of the microcapsule.
13. The microcapsules according to any of the embodiments 1 to 12, additionally comprising water, preferably in an amount of less than 60% by weight, more preferably less than 50% by weight, more preferably less than 40% by weight, more preferably less than 35% by weight, based on the total weight of the microcapsules.
14. The microcapsules according to any of the embodiments 1 to 13, wherein the polymeric coating is crosslinked with the matrix via electrostatic interactions.

15. The microcapsules according to any of the embodiments 1 to 14, wherein the polysaccharides present in the matrix are crosslinked with each other and/or with themselves via metal ions, preferably via calcium and/or zinc ions.
16. The microcapsules according to any of the embodiments 1 to 15, comprising calcium chloride.
17. The microcapsules according to embodiment 16, wherein the polysaccharide comprised in the matrix is anionic and the polymer comprised in the coating is cationic and wherein the the polysaccharide comprised in the matrix and polymer comprised in the coating are crosslinked via electrostatic interactions.
18. The microcapsules according to any of the embodiments 1 to 17, having a mean particle size in the range of from 0.1 to 5 mm, more preferably in the range of from 0.8 to 1.5 mm, more preferably in the range of from 1.1 to 1.3 mm, measured using a digital caliper.
19. The microcapsules according to any of the embodiments 1 to 18, wherein the polymeric coating comprises a polymer selected from the group consisting of poly-amino saccharides, methyl acrylate-methacrylic acid copolymers, methyl methacrylate-methacrylic acid copolymers, pectins, alginates, carrageenans, xanthan, gellan, tragacanth, hyaluronic acid, gums, celluloses, starches, agar, arabinoxylans, curdlan, beta-glucan, glucomannans, pullulan, chondroitin sulfate, dextrans, aminodextran, dimethylaminodextran, cellulose acetate succinate, hydroxy propyl methyl cellulose phthalate, hydroxy propyl methyl cellulose acetate succinate, and derivatives thereof.
20. The microcapsules according to any of the embodiments 1 to 19, wherein the polymeric coating is essentially not digestible by human enzymes present in the upper gastrointestinal tract.
21. The microcapsules according to any of the embodiments 1 to 20 being adapted so that the active agent is not released in the upper gastrointestinal tract.
22. The microcapsules according to any of the embodiments 1 to 21, being adapted so that release of the active agent takes place in the colon.
23. The microcapsules according to any of the embodiments 1 to 22, wherein the polymeric coating comprises a poly-amino saccharide, preferably chitosan.
24. A method for preparing microcapsules comprising a polymeric coating, the polymeric coating being at least partly crosslinked with a polymeric matrix comprising a second polysaccharide, wherein in the matrix a lipid and an active agent or a prodrug or salt thereof are embedded, the lipid having a melting point of at least 30° C., the method comprising
    (a) providing an aqueous solution comprising the polymer being comprised in the coating
    (b) providing an aqueous composition comprising the polysaccharide,
    (c) forming an oil phase comprising the lipid and the active agent or prodrug or salt thereof, preferably by heating the oil phase to the melting temperature of the lipid or above, preferably for a time in the range of from 1 min to 1 h,
    (d) mixing the oil phase according to (c) with the aqueous phase according to (b) thereby forming an emulsion,
    (e) adding the emulsion according to (d) drop-wise to the solution according to (a) thereby forming the microcapsule,
    (f) isolating the microcapsules and drying of the isolated microcapsules.
25. The method according to embodiment 24, wherein the oil phase is heated to a temperature in the range of from 50 to 70° C., preferably to around 60° C. for a time in the range of from 30 s to 1 min prior to step (d).
26. The method according to embodiment 24 or 25, wherein step (a) further comprises adding at least one metal salt, preferably calcium chloride to the solution prior to step (e).
27. The method according to any of the embodiments 24 to 26, wherein step (a) further comprises adjusting the pH of the solution to a pH of from 1 to 6, preferably with acetic acid.
28. The method according to any of the embodiments 24 to 27, wherein the oil phase according to (c) further comprises lecithin.
29. The method according to any of the embodiments 24 to 28, wherein the drying in (f) is carried out at a temperature in the range of from 25° C. to 80° C. for a time in the range of from 1 minute to 96 hours, preferably 1 h to 48 h.
30. The method according to any of the embodiments 24 to 29, wherein the drop-wise addition in step (e) is carried out manually using a syringe or by means of a droplet generating device such as a jet-cutter.
31. Microcapsules obtained or obtainable by the method according to any of the embodiments 24 to 30.
32. Microcapsules according to any of the embodiments 1 to 23 or 31 for use as a medicament.
33. Microcapsules according to any of the embodiments 1 to 23 or 31 for use in preventing and/or treating of colon cancer and/or for use in preventing and/or treating of diarrhoea.
34. Use of the microcapsules according to any of the embodiments 1 to 23 or 31 as dietary supplement or food additive.
35. The microcapsules according to any one of embodiments 32 to 34, wherein the microcapsules are administered orally or via a feeding-tube.
36. A method for treating diarrhoea or preventing colon cancer comprising administering at least one microcapsule according to any one of embodiments 1 to 23 or 31 to a patient in need thereof.
37. The method according to embodiment 36, wherein the at least one microcapsule is administered orally.
38. A container comprising:
    a container body defining a container chamber holding a liquid and comprising an opening,
    a container cap mounted at the opening of the container body, wherein the container cap comprises a dispensing mechanism comprising a closed end, an open end and a cap chamber defined therebetween holding at least one microcapsule according to any one of embodiments 1 to 23 or 31, wherein the dispensing mechanism is movable between a storage position, wherein the cap chamber is sealed off from the container chamber, and an activated position, wherein the microcapsule is allowed to be dispensed into the container chamber.
39. The container according to embodiment 38, further comprising a sealing member disposed adjacent the open end.
40. The container according to embodiment 39, wherein the sealing member is adapted to be removed from the open end if the dispensing mechanism is moved to the activated position.
41. The container according to embodiment 39 or 40, wherein the sealing member is integrally formed with the dispensing mechanism.

42. The container according to embodiment 39 or 40, wherein the sealing member is separately formed from the dispensing mechanism.
43. The container according to any one of embodiments 38 to 42, wherein the dispensing mechanism is a plunger adapted to be linearly moveable between the storage position and the activated position.
44. The container according to any one of embodiment 38 to 43, wherein the dispensing mechanism is a knob adapted to be rotated.
45. The container according to any one of embodiments 39 to 44, wherein the sealing member is adapted to be broken if the dispensing mechanism is moved to the activated position.
46. The container according to embodiment 44, wherein the knob comprises a blade member adapted to cut the sealing member if the dispensing mechanism is moved to the activated position.
47. Use of the container according to any one of embodiments 38 to 46 for providing a liquid dispensed composition, comprising the steps:
   (i) providing the container body with the container chamber holding a liquid,
   (ii) mounting the cap to the opening of the container body with the cap chamber holding at least one microcapsule, and
   (iii) activating the dispensing mechanism so as to move from the storage position to the activated position such that at least one microcapsule is dispensed into the container chamber of the container body so as to form the liquid dispensed composition.
48. Use of the container for providing a liquid dispensed composition according to embodiment 47 wherein the dispensing mechanism is activated by means of a linear or rotational force.
49. Use of the container for providing a liquid dispensed composition according to embodiment 47 or 48, wherein the cap is removed after activating the dispensing mechanism.
50. Use of the container for providing a liquid dispensed composition according to any one of embodiments 47 to 49, wherein the liquid dispensed composition is adapted to be orally administered.
51. Use of the container for providing a liquid dispensed composition according to any one of embodiments 47 to 50, wherein the liquid dispensed composition is adapted to be drunk from the container by a patient in need thereof.
52. A container cap adapted to be mounted at an opening of a container body, wherein the container cap comprises a dispensing mechanism comprising a closed end, an open end and a cap chamber defined therebetween holding at least one microcapsule according to any one of embodiments 1 to 23 or 31, wherein the dispensing mechanism is movable between a storage position, wherein the cap chamber is sealed off, and an activated position, wherein the microcapsule is allowed to be dispensed from the cap chamber.
53. The container cap according to embodiment 52, further comprising a sealing member disposed adjacent the open end.
54. The container cap according to embodiment 53, wherein the sealing member is adapted to be removed from the open end if the dispensing mechanism is moved to the activated position.
55. The container cap according to embodiment 53 or 54, wherein the sealing member is integrally formed with the dispensing mechanism.
56. The container cap according to embodiment 53 or 54, wherein the sealing member is separately formed from the dispensing mechanism.
57. The container cap according to any one of embodiments 52 to 56, wherein the dispensing mechanism is a plunger adapted to be linearly moveable between the storage position and the activated position.
58. The container cap according to any one of embodiment 52 to 56, wherein the dispensing mechanism is a knob adapted to be rotated.
59. The container cap according to any one of embodiments 52 to 58, wherein the sealing member is adapted to be broken if the dispensing mechanism is moved to the activated position.
60. The container cap according to embodiment 59, wherein the knob comprises a blade member adapted to cut the sealing member if the dispensing mechanism is moved to the activated position.

FIGURES

The scope of the invention is not restricted by the figures. Some embodiments are only schematically depicted in the figures. Therein, identical reference numbers in these figures refer to identical or functionally comparable elements.

Figure 4:
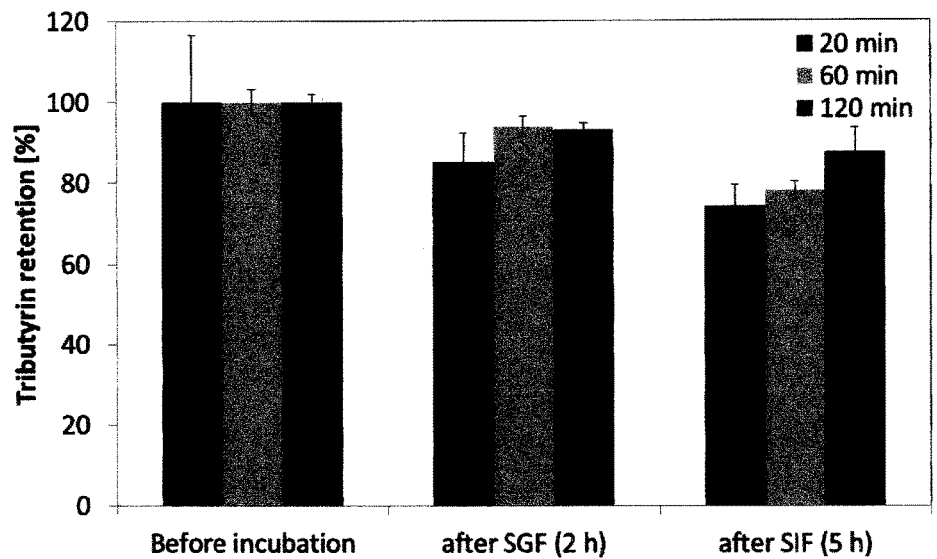

FIG. 1 shows a cross-sectional view of a container according to a first embodiment of the present invention, FIG. 2 shows an enlarged partial cross-sectional view of the container according to the first embodiment of the present invention, FIG. 3 shows an enlarged partial cross-sectional view of a container according to a second embodiment of the present invention FIG. 4 shows the influence of crosslinking time on tributyrin retention of microcapsules during successive incubation in simulated gastric fluid (SGF, 2 h, pH 3) and simulated intestinal fluid (SIF, 3 h, pH 6.5); Mean microcapsule diameter=1.11 mm, Drying of microcapsules at 30° C.

Figure 5:
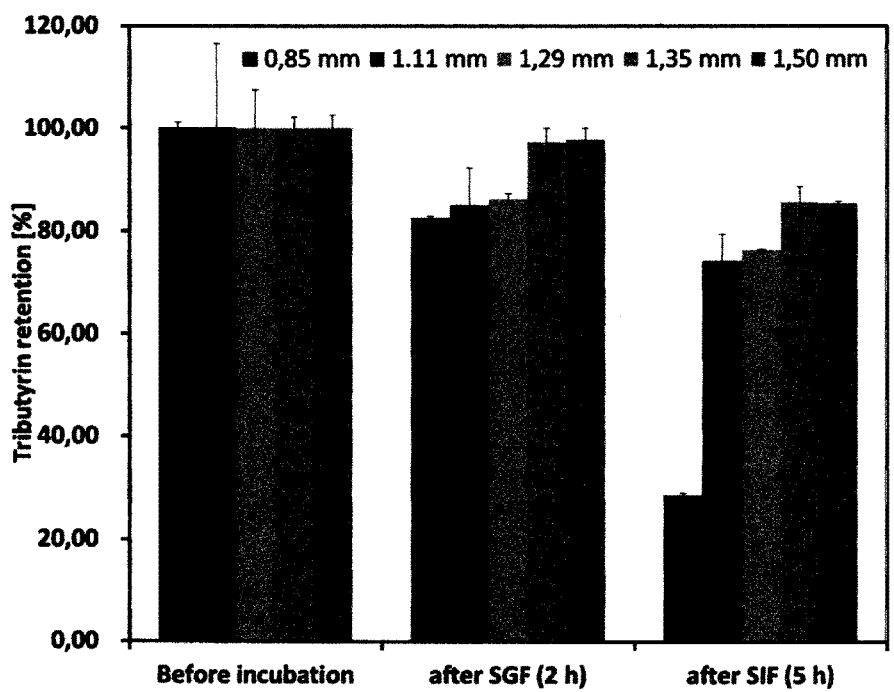

FIG. 5 shows the influence of microcapsule diameter on tributyrin retention of microcapsules during successive incubation in simulated gastric fluid (SGF, 2 h, pH 3) and simulated intestinal fluid (SIF, 3 h, pH 6.5). Drying of microcapsules at 30° C.

Figure 6:
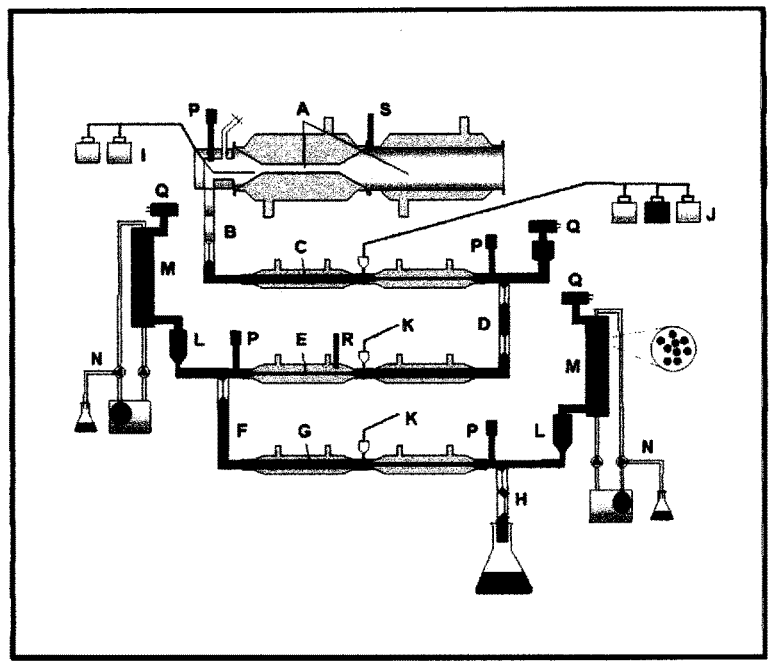

FIG. 6 shows the schematic depiction of the TNO TIM 1 water system for the simulation of the upper gastrointestinal tract (stomach and small intestine). The following abbreviations are used: A. stomach compartment, B. pyloric sphincter, C. duodenal compartment, D. peristaltic valve, E. jejunum compartment, F. peristaltic valve, G. ileum compartment, H. ileo-caecal sphincter, I. stomach secretion bottles with acid and enzymeS, J. duodenal secretion bottles with bile pancreatin, bicarbonate, K. secretion of bicarbonate to control the intestinal Ph, L. pre-filter, M. hollow fiber semi-permeable membrane system semi-permeable membrane, N. water absorption system filtrate pump, P. pH control, Q. volume control. R. temperature control, S. pressure control.

Figure 7:
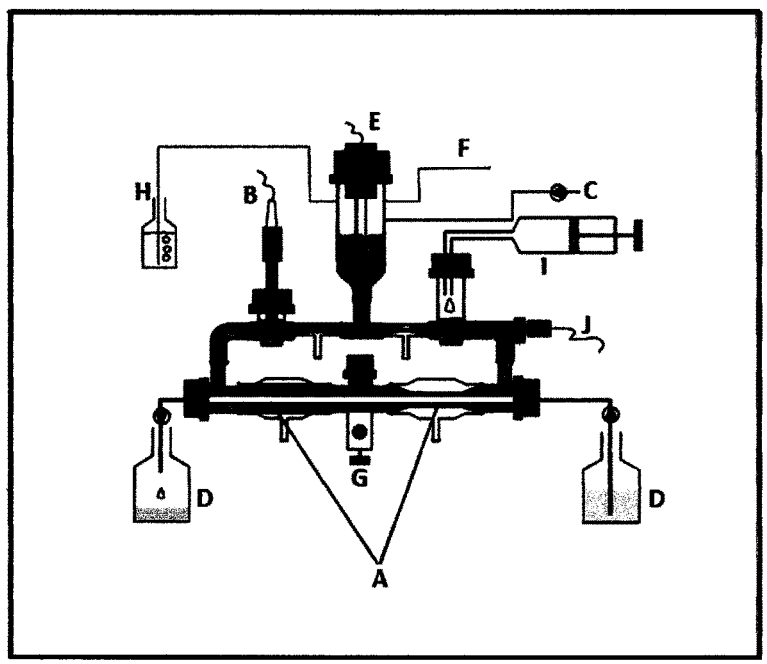

FIG. 7 shows the schematic depiction of the TNO TIM-2 system for the simulation of the lower gastrointestinal tract (colon): The following abbreviations are used: (A) peristaltic compartments containing fecal matter; (B) pH electrode; (C) alkali pump; (D) dialysis liquid circuit with hollow fibre membrane; (E) level sensor; (F) N2 gas inlet; (G) sampling port; (H) gas outlet; (I) 'ileal efflux' container; (J) temperature sensor.

Figure 8:
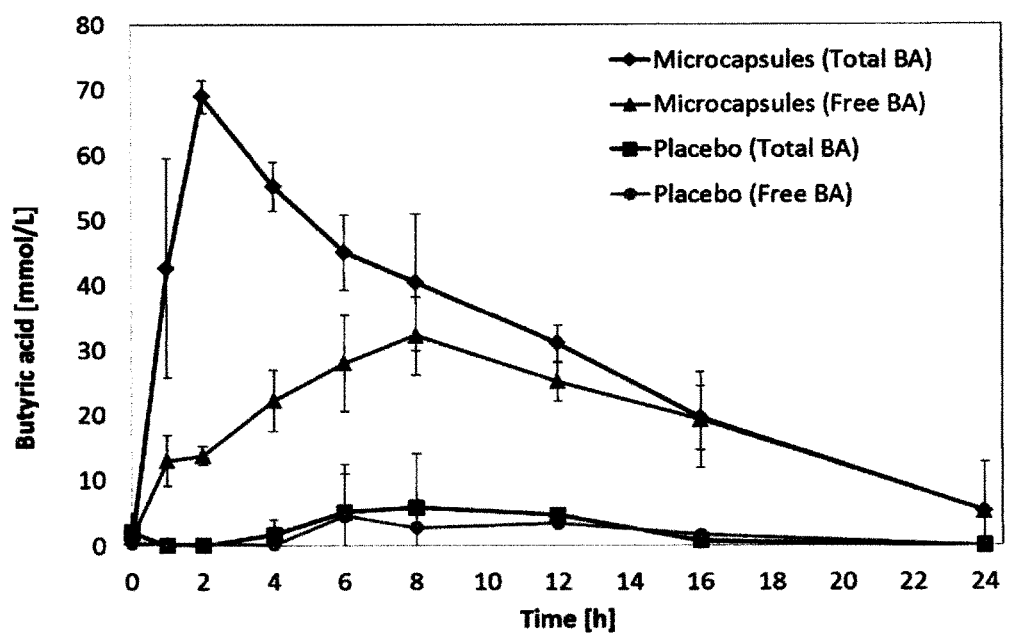

FIG. 8 shows the concentration of free butyric acid and total butyric acid (free butyric acid and tributyrin) in the TNO TIM-2 lumen during incubation of microcapsules (predigested in TNO TIM-1) with encapsulated tributyrin or without encapsulated tributyrin (Placebo). The depicted values are corrected for the blank values of the TIM-2 system.

EXAMPLES

Example 1

General Procedure A for the Preparation of the Microcapsules a) Preparation of the Oil Phase and Determination of Optimum Oil Phase Composition The oil phase was prepared by mixing the lipid with tributyrin and heating the mixture to 60° C. to melt the respective lipid if the lipid was solid at room temperature. Afterwards, lecithin was optionally added and dissolved during stirring using a small spoon, wherein the mixture was heated to 60° C. if necessary to dissolve the lecithin. For preparation of microcapsules the oil phase was used at 60° C. without cooling.

b) Preparation of the Water Phase

Pectin powder was added slowly during stirring using an Ultra-Turrax® T 25 at maximum speed to hot water which was preheated to above 90° C. using a water boiler. The mixing was carried out until the mixture was homogenous. The homogenous solution was then placed on a heating plate (150° C.) and heated to boiling temperature and boiled for 5 min, wherein the mixture was stirred using a magnetic stirrer during the heating. The total weight of the solution was checked and, if necessary, evaporated water was replaced.

c) Preparation of the Oil-in-water Emulsion

The water phase was stirred using an Ultra-Turrax® T 25 stirrer at 60° C. and the oil phase was heated to 60° C. and then added to the water phase during stirring. The stirring was carried out using an Ultra-Turrax® T 25 stirrer for 5 min at 24,000 rpm at 60° C. Afterwards, the generated emulsion was cooled down to ambient temperature, i.e. 20° C. to 25° C. without stirring.

d) Preparation of the Crosslinking Solution

Chitosan powder was dispersed in a 1% aqueous solution of acetic acid. The dispersion was heated to 70° C. during stirring until chitosan was fully dissolved. Calcium chloride was dissolved in deionised water. Calcium chloride solution was added to the chitosan solution during stirring and pH of final mixture was adjusted to the desired value using acetic acid or NaOH.

e) Generation of the Microcapsules, Crosslinking and Drying

The generated oil-in-water emulsion was dropped manually using a pipette to a crosslinking solution at 20° C. to 25° C. during stirring with a magnetic stirrer. The droplets were kept inside the crosslinking solution to solidify them by ionotropic gelation.

After removal of the gelled droplets (microcapsules), the microcapsules were rinsed with deionized water and dried with tissue paper. Afterwards, the microcapsules were dried in a drying oven until the mass was constant. The microcapsules were stored in an airtight plastic container until they were further used.

f) Determination of Tributyrin Content

The tributyrin content in the microcapsules was determined as butyric acid after disintegration of microcapsules followed by saponification and derivatisation, separation by HPLC and photometric detection, as described in detail hereafter:

For the determination of the total butyric acid (=free butyric acid and butyric acid from tributyrin), the microcapsules were transferred to potassium hydroxide solution and stirred for 12 h at ambient temperature to achieve their disintegration. The obtained solution was heated to 80° C. for 20 min to achieve saponification of the tributyrin. The obtained free butyric acid was then derivatised using 2-Nitrophenylhydrazinhydrochlorid. The derivatised butyric acid was extracted by diethyl ether and dissolved in methanol, submitted to HPLC (C8-column) and detected photometrically at 400 nm. HPLC-mobile phase consisted of diluted hydrochloric acid at pH 4.5 (Eluent A) and a 40% methanol/60% acetonitrile-mixture (Eluent B). The following gradient was used: 0 min (50% A, 50% B), 20 min (50% A, 50% B), 27 min (100% B), 30 min (100% B), 37 min (50% A, 50% B), 40 min (50% A, 50% B). Pentanoic acid was used as internal standard.

For the determination of free butyric acid (butyric acid in the form of tributyrin was not detected in this case) the microcapsules were disintegrated in diluted hydrochloric acid (without saponification of tributyrin) followed by derivatisation and detection as described above.

Example 2

Determination of the Optimum Oil Phase Composition

The oil phase was prepared according to the general procedure A wherein the lipid L in an amount of X was mixed with liquid tributyrin in an amount Y. It was desired to obtain a solid oil phase at ambient temperature in order to achieve a physical entrapment of the tributyrin within a solid oil phase.

For identifying a suitable oil phase composition, the prepared differently composed oil phases were cooled to ambient temperature and their physical state was recorded as summarized in table 1.

Table 1 shows that no solidification of the oil phase could be obtained within the investigated concentration ranges when tributyrin was mixed with sunflower oil. However, when a solid hydrogenated coconut kernel oil (Witocan 42/44) was mixed with the tributyrin, a solidification of the oil phase could be achieved upon cooling at a concentration of 19% Witocan and above.

Example 3.

Determination of the Optimum Amount of Lipid in the Microcapsules

With regard to handling, it was desired to obtain non-sticky, free-flowing microcapsules showing an effective entrapment of the tributyrin-containing oil phase (no oil-leakage was desired).

Microcapsules with varying lipid content were prepared according to the general procedure A having a composition according to entries 1 to 11 in table 2. Drying was carried out at 30° C. The mean diameter of the microcapsules was 1.3 mm. The dried microcapsules were visually examined with respect to their free flowing behavior and possible oil leakage out of the microcapsules. As may be taken from the results summarized in table 2, in particular the microcapsules with a pectin concentration in the emulsion of around 4% and a lipid phase content in the emulsion of around 4% to 5% turned out to be particularly advantageous with respect to their free flowing behavior, i.e. their non-stickiness. Further they showed no oil leakage out of the microcapsules. It has to be mentioned that this selection of a composition was done considering handling as main criterion. However, with regard to the criterion of colon-targeting, the other microcapsules tested are likewise suitable.

Example 4

Crosslinking Conditions to Generate Microcapsules a) Preparation of the Microcapsules
The microcapsules were prepared according to the general procedure A, wherein different crosslinking conditions and different pectins in the emulsion were used. (See table 3)
According to table 3, crosslinking conditions varied in crosslinking time, crosllinking pH and the type of chitosan (DD=Degree of Deacetylation; η=Viscosity in mPas). In addition the type of pectin in the emulsion (DE=Degree of Esterification, DA=Degree of Amidation) was varied.
The crosslinking solution contained 1% w/w chitosan and 5% zinc acetate or 5% calcium chloride. Microcapsules could be prepared at all investigated crosslinking conditions according to table 3. The crosslinking conditions as described in A, B and C were chosen for the preparation of microcapsules for further tests.

Example 5

Determination of the Impact of Diameter and Crosslinking Time on the Stability of the Microcapsules and of Tributyrin Retention within the Microcapsules During Incubation in Simulated Gastric Fluid and Simulated Intestinal Fluid a) The microcapsules were prepared according to the general procedure A. Microcapsules with a mean diameter of 1.3 mm were prepared under the crosslinking conditions A, B and C (using calcium chloride as bivalent cation) according to example 3. The emulsion contained 4% w/w pectin and 4% oil phase. In addition microcapsules with mean diameters of 0.85 mm, 1.11 mm, 1.35 mm and 1.5 mm were prepared at crosslinking conditions C (using calcium chloride instead) according to example 3. Drying was carried out at 30° C.
Digestive media with a composition according to table 4 were prepared
1. Preparation of simulated digestive media
   a. Simulated Gastric Fluid (SGF) at pH 3.0 was prepared by dissolving the individual compounds in water and adjusting the pH to 3.0 using NaOH and HCl.
   b. Simulated Intestinal Fluid (SIF) at pH 6.5 was prepared by dissolving the individual compounds in water and adjusting the pH to 6.5 using NaOH and HCl.
2. Incubation of microcapsules in the digestive media
   a. 0.1 g of dried microcapsules were added to 20 ml of simulated gastric fluid and incubated at 37° C. during shaking
   b. After 2 h in SGF the microcapsules were transferred to 20 ml SIF for further 3 h at 37° C. during shaking.
   c. Total tributyrin content of microcapsules was determined after 2 h in SGF and after 3 h in SIF using the HPLC-method described above.

FIG. 4 shows the impact of crosslinking time on tributyrin retention within microcapsules during incubation in simulated digestive media. At all crosslinking times a high tributyrin retention of more than 75% could be achieved after the incubation in the digestive media. A disintegration or loss of microcapsules was not observed during the experiments indicating a high stability independent of which crosslinking time was used.

FIG. 5 shows the impact of microcapsule diameter on the tributyrin retention within the microcapsules during incubation in simulated digestive media. A larger microcapsule diameter was particularly advantageous with regard to the retention of tributyrin within the microcapsules. Under simulated intestinal conditions (SIF) a small diameter of 0.85 mm was accompanied by a lower tribuytrin retention.

Example 6

Stability of Microcapsules and Tributyrin Retention within Microcapsules during Simulated Digestion of the Microcapsules a) Preparation of the Microcapsules
The microcapsules were prepared according to the general procedure A (example 1) under crosslinking conditions C (table 3, using calcium chloride instead of zinc acetate) according to example 4. Mean diameter of microcapsules was 1.1 mm. Drying was carried out a 50° C. Placebo microcapsules were prepared by replacing tributyrin in the oil phase by corn oil.
b) Description of the Dynamic in-vitro Gastrointestinal Tract Systems used to for Simulated Digestion of the Microcapsules
The studies were performed in the TNO dynamic, multi-compartmental systems of the stomach and small intestine (TIM-1) and colon (TIM-2) schematically presented in FIG. 6 (TIM-1) and FIG. 7 (TIM-2). The TIM-1 model simulates very closely the successive dynamic conditions in the gastric-small-intestinal tract. such as body temperature, the pH curves, concentrations of electrolytes, and the activity of enzymes in the stomach and small intestine, the concentrations of bile salts in the different parts of the gut, and the kinetics of transit of the chyme through the stomach and small intestine. The TIM-2 model simulates the successive dynamic anaerobic conditions in the proximal, transverse, and distal colon. It is inoculated with standardised stools, pooled from healthy human volunteers on a 'general' Western type of diet. Both systems simulate the peristaltic and the absorption of low molecular molecules (whether or not incorporated within mixed micelles), and water using hollow fibre membranes (cf JP, US, European Patent PCT/NL93/00225, 1994.)
c) Constituents of the Simulated Gastric Fluids that were used in the Different Compartments of the TNO TIM-1-system:
Composition of the simulated digestive media of the TNO TIM-1 model was according to table 4.

d) Performance of the Simulated Digestion of the Microcapsules using the TNO TIM-1 System and the TNO TIM-2 System The microcapsules were incubated in the TNO TIM-1 system containing simulated digestive media
  a. Preparation of the TNO TIM-1 system: filling with digestive media, preheating to 37° C., pH-values at start:
    stomach=5.5
    duodenum=5.9
    jejunum=6.5
    ileum=7.4
    Preparation of the TNO TIM-2 system:
    Inoculation at 37° C. with standardised stools, pooled from healthy human volunteers (5 to 6 healthy volunteers) on a 'general' Western type of diet and no intake of drugs during the last 10 days
    pH-values during run:
    0 h=5.8
    8 h=6.8
    16h=7.0
    24 h=7.2
  b. Addition of 7 g of microcapsules to the TNO TIM-1 stomach and starting of digestion protocol (gastric emptying time: 40 min).
  c. Collection of ileum efflux (sample that is released by the system) during 150 min.
  d. Harvesting of microcapsules from the ileum efflux and determination of tributyrin content of microcapsules by HPLC.
  e. Transfer of 19 g microcapsules (corresponds to 5 g dried microcapsules) that were harvested from TNO TIM-1 ileum efflux to the TNO TIM-2 system (two 9.5 g shots at 0 min and 30 min, mimicking a gradual arrival of microcapsules in the colon).
  f. Sampling of TNO TIM-2 lumen and dialysate samples after defined time intervals and analysis of content of free butyric acid and tributyrin.

The results of the simulated gastric and small intestinal digestion of the microcapsules are depicted in table 5 (TNO TIM-1). The comparison of the number of microcapsules before and after the simulated digestion, as shown in table 5, indicates a high resistance of the microcapsules' matrix against the simulated gastric and small intestinal conditions in the TIM-1 system. In addition, the tributyrin content of the microcapsules was not affected by the simulated digestion. These results give rise to the conclusion that the microcapsules are capable of targeting the colon after being administered orally.

The microcapsules that were recovered from the simulated upper gastrointestinal tract (ileum efflux of the TIM-1 system) were transferred to the TIM-2 system to evaluate their stability under simulated colonic conditions. It was found that the microcapsules were completely disintegrated in the colonic environment within 4 hours and the encapsulated tributyrin was released during that time.

FIG. 8 shows the time-dependent concentration of free butyric acid and total butyric acid (free butyric acid and tributyrin) in the colon-lumen of the TIM-2 system after the incubation of the microcapsules. There was no difference between the curves for the free butyric acid and total butyric acid that was released from the placebo-microcapsules. As the placebos did not contain tributyrin, only the butyric acid that was formed by microbial fermentation of the constituents of the microcapsules' matrix could be determined.

This was not the case for the tributyrin-containing microcapsules. Due to the disintegration of the microcapsules the tributyrin was released within the first two hours, leading to a strong increase of total butyric acid. At the same time, the released tributyrin was cut down to free butyric acid by microbial enzymes which is reflected by the ascending free butyric acid curve and the at the same time descending free butyric acid curve. When all the tributyrin was transformed to free butyric acid, both curves coincided after 12 hours. Conclusively, these results show that the microcapsules were disintegrated in the colonic environment and the contained tributyrin was released in the colonic lumen as desired.

TABLE 1

Physical state of differently composed oil phases

| Oil Phase | Lipid L | Amount X [%] | Amount Y (Tributyrin) [%] | Amount Z (Lecithin) [%] | Physical state of oil phase at 20° C. |
|---|---|---|---|---|---|
| A | Corn oil | 20 | 80 | 0 | liquid |
| B | Witocan 42/44 | 20 | 80 | 0 | solid |
| C | Corn oil | 19 | 75 | 6 | liquid |
| D | Witocan 42/44 | 19 | 75 | 6 | solid |
| E | Corn oil | 10 | 90 | 0 | liquid |
| F | Corn oil | 35 | 65 | 0 | liquid |
| G | Corn oil | 50 | 50 | 0 | liquid |
| H | Witocan 42/44 | 10 | 90 | 0 | liquid |
| I | Witocan 42/44 | 35 | 65 | 0 | solid |
| J | Witocan 42/44 | 50 | 50 | 0 | solid |

TABLE 2

Properties of microcapsules with varying oil phase content

| Oil in water Emulsion | Oil Phase | Oil phase content in emulsion [%] | Pectin concentration in emulsion [%] | Crosslinking solution | Visual examined properties |
|---|---|---|---|---|---|
| 1 | C | 30 | 2 | C | oil leakage/sticky |
| 2 | C | 20 | 2 | C | oil leakage/sticky |
| 3 | C | 20 | 4 | C | No oil leakage/sticky |
| 4 | C | 10 | 4 | C | No oil leakage/sticky |
| 5 | D | 10 | 4 | C | No oil leakage/sticky |
| 6 | D | 6 | 4 | C | No oil leakage/sticky |
| 7 | D | 5.3 | 3.8 | C | No oil leakage/non-sticky |
| 8 | D | 5.3 | 3.8 | C | No oil leakage/non-sticky |
| 9 | C | 5 | 4 | C | No oil leakage/non-sticky |
| 10 | C | 5 | 4 | C | No oil leakage/non-sticky |
| 11 | D | 4 | 4 | C | No oil leakage/non-sticky |

TABLE 3

Crosslinking conditions and pectin types suitable for the preparation of microcapsules.

| | A | B | C | D | E | F | G |
|---|---|---|---|---|---|---|---|
| Pectin (DA/DE) | 22/29 | 22/29 | 22/29 | 22/29 | 22/29 | 22/29 | 25/25 |
| Chitosan (DD/η) | 85/100 | 85/100 | 85/100 | 85/5 | 95/5 | 95/100 | 85/100 |
| pH | 3.5 | 3.5 | 3.5 | 3.5 | 3.5 | 3.5 | 3.0 |
| Crosslinking time (min) | 60 | 40 | 20 | 20 | 20 | 20 | 20 |

TABLE 4

Composition of the simulated digestive media.

| Compound | Unit | Simulated gastric fluid (SGF) | Simulated intestinal fluid (SIF) |
|---|---|---|---|
| Sodium chloride | % w/w | 0.210 | 0.123 |
| Potassium chloride | % w/w | 0.074 | 0.015 |
| Calcium chloride dihydrate | % w/w | 0.010 | 0.007 |
| Bile porcine powder (Sigma B-8631) | % w/w | — | 1.892 |
| Pancrex-vet powder (Pfizer) | % w/w | — | 1.609 |
| Rhizopus lipase F-AP15 (Amano Ph.) | units/g | 1 | — |
| Pepsin (Sigma P-7012) | units/g | 10 | — |
| α-Amylase (Sigma A-6380) | units/g | 55 | — |
| Trypsin (Sigma T-9201) | units/g | — | 246 |

TABLE 5

Number of microcapsules and tributyrin content of tributyrin-containing microcapsules (Test) and microcapsules without tributyrin (Placebo) before and after simulated gastric and small intestinal digestion using the TNO TIM-1 model.

| Parameter | Sample | Before TIM-1 | After TIM-1 |
|---|---|---|---|
| Number of microcapsules [—] | Placebo 1 | 4886 ± 74 | 4788 ± 82 |
| | Placebo 2 | 4997 ± 100 | 4993 ± 83 |
| | Test 1 | 5893 ± 86 | 5347 ± 141 |
| | Test 2 | 5450 ± 102 | 5469 ± 127 |
| Tributyrin content per microcapsule [mg] | Placebo 1 | — | — |
| | Placebo 2 | — | — |
| | Test 1 | 0.32 ± 0.02 | 0.34 ± 0.02 |
| | Test 2 | 0.37 ± 0.02 | 0.39 ± 0.02 |

The invention claimed is:

1. A microcapsule comprising a polymeric coating and a polymeric matrix comprising a polysaccharide,
   wherein the polymeric coating is at least partly cross-linked with the polymeric matrix;
   wherein a lipid and an active agent or a prodrug or salt thereof are embedded in the matrix, wherein the lipid has a melting point of at least 30° C.;
   wherein said microcapsule comprises the lipid in an amount of from 0.2 to 72% by weight;
   wherein the lipid and the active agent or the prodrug or salt thereof is present in said microcapsule in a weight ratio of from 1:9 to 9:1;
   wherein the lipid is chosen from hydrogenated coca-glycerides; and
   wherein the microcapsule does not leak oil and is non-sticky.

2. The microcapsule according to claim 1, wherein the polysaccharide is selected from the group consisting of pectins, alginates, carrageenans, xanthan, gellan, tragacanth, hyaluronic acid, gums, celluloses, starches, agar, arabinoxylans, curdlan, beta-glucan, glucomannans, pullulan, chondroitin sulfate, dextrans, chitosans, aminodextran and dimethylaminodextran and derivatives of the aforementioned polysaccharides.

3. The microcapsule according to claim 1, wherein the embedded lipid has a melting point of from 30° C. to 80° C., and wherein the lipid crystallizes upon cooling in the beta prime crystal form.

4. The microcapsule according to claim 1, wherein the active agent is butyric acid or a prodrug or salt thereof.

5. The microcapsule according to claim 1, wherein the polymeric coating is crosslinked with the matrix via electrostatic interactions, wherein the polysaccharide comprised in the matrix is a cationic polysaccharide or an anionic polysaccharide and the polymer present in the polymer comprised in the polymeric coating is the opposite that is either anionic or cationic.

6. The microcapsule according to claim 1, wherein the polysaccharide present in the matrix is crosslinked with itself and/or with itself via metal ions.

7. The microcapsule according to claim 1, having a mean particle size in the range of from 0.1 to 5 mm, measured using a digital caliper.

8. The microcapsule according to claim 1, wherein the polymeric coating is essentially not digestible by human enzymes present in the upper gastrointestinal tract.

9. The microcapsule according to claim 1, being adapted so that the active agent is not released in the upper gastrointestinal tract.

10. The microcapsule according to claim 1, being adapted so that release of the active agent takes place in the colon.

11. The microcapsule according to claim 1, wherein the polymeric coating comprises a poly-amino saccharide.

12. A method for preparing the microcapsule according to claim 1, the method comprising
   (a) providing an aqueous solution comprising the polymer being comprised in the coating,
   (b) providing an aqueous composition comprising the polysaccharide,
   (c) forming an oil phase comprising the lipid and the active agent or prodrug or salt thereof,
   (d) mixing the oil phase according to (c) with the aqueous phase according to (b) thereby forming an emulsion,
   (e) adding the emulsion according to (d) drop-wise to the solution according to (a) thereby forming the microcapsule, and
   (f) isolating the microcapsules and drying of the isolated microcapsules.

13. The method according to claim 12, wherein step (a) further comprises adding at least one metal salt to the solution prior to step (e).

14. A microcapsule comprising a polymeric coating, the polymeric coating being at least partly crosslinked with a polymeric matrix comprising a polysaccharide, wherein a lipid having a melting point of at least 30° C. and an active agent or a prodrug or salt thereof are embedded in said matrix, which is obtained or obtainable by a method comprising
  (a) providing an aqueous solution for coating said microcapsule with a polymeric coat, wherein said aqueous solution comprises a polymer being comprised in the coating,
  (b) providing an aqueous composition comprising the polysaccharide,
  (c) forming an oil phase comprising the lipid having a melting point of at least 30° C. and the active agent or prodrug or salt thereof by heating the oil phase to the melting temperature of the lipid or above,
  (d) mixing the oil phase according to (c) with the aqueous composition according to (b), thereby forming an emulsion,
  (e) adding the emulsion according to (d) drop-wise to the aqueous solution according to (a), thereby forming the microcapsule, optionally adding the microcapsule to a crosslinking solution, and
  (f) isolating the microcapsule and drying the isolated microcapsule,
  wherein the lipid is chosen from hydrogenated coca-glycerides; and
  wherein the obtained microcapsule does not leak oil and is non-sticky.

15. A method of treating colon cancer and/or treating diarrhea, the method comprising administering to a patient in need thereof, the microcapsule according to claim 1.

16. A dietary supplement or food additive comprising the microcapsule according to claim 1.

17. The microcapsule according to claim 1, wherein said hydrogenated coco-glyceride has from 10-18 carbon atoms.

18. The microcapsule according to claim 1, wherein the lipid has a melting point in the range of from 42° C. to 44° C.

19. The microcapsule according to claim 1, wherein at least 95% of the coating consists of a polymer selected from the group consisting of chitosan, poly-amino saccharides, methyl acrylate-methacrylic acid copolymers, cellulose acetate succinate, hydroxy propyl methyl cellulose phthalate, hydroxy propyl methyl cellulose acetate succinate, methyl methacrylate-methacrylic acid copolymers, and sodium alginate, and mixtures of two or more thereof; and
  wherein the polysaccharide in the polymeric matrix comprises one or more polysaccharides selected from the group consisting of pectins, alginates, carrageenans, xanthan, gellan, tragacanth, hyaluronic acid, gums, celluloses, starches, agar, arabinoxylans, curdlan, beta-glucan, glucomannans, pullulan, chondroitin sulfate, dextrans, chitosans, aminodextran and dimethylamino-dextran and derivatives of the aforementioned polysaccharides.

* * * * *